(12) United States Patent
Balasa et al.

(10) Patent No.: US 7,935,793 B2
(45) Date of Patent: May 3, 2011

(54) TREATMENT OF INFLAMMATORY BOWEL DISEASES WITH ANTI-IP-10 ANTIBODIES

(75) Inventors: Balaji Balasa, Union City, CA (US); Naoya Tsurushita, Palo Alto, CA (US); Nicholas F. Landolfi, Menlo Park, CA (US)

(73) Assignee: Abbott Biotherapeutics Corp., Redwood City, CA (US)

( * ) Notice: Subject to any disclaimer, the term of this patent is extended or adjusted under 35 U.S.C. 154(b) by 365 days.

(21) Appl. No.: 10/581,468

(22) PCT Filed: Nov. 10, 2004

(86) PCT No.: PCT/US2004/037600
§ 371 (c)(1),
(2), (4) Date: May 4, 2007

(87) PCT Pub. No.: WO2005/060457
PCT Pub. Date: Jul. 7, 2005

(65) Prior Publication Data
US 2008/0063646 A1    Mar. 13, 2008

Related U.S. Application Data

(60) Provisional application No. 60/527,882, filed on Dec. 4, 2003.

(51) Int. Cl.
*C07K 16/24* (2006.01)
*A61K 39/395* (2006.01)

(52) U.S. Cl. .................. 530/387.9; 424/139.1

(58) Field of Classification Search .................. None
See application file for complete search history.

(56) References Cited

U.S. PATENT DOCUMENTS

| 4,719,107 A * | 1/1988 | Carosella et al. .......... 424/130.1 |
| 4,762,027 A | 8/1988 | Fagiolini et al. |
| 7,297,478 B1 * | 11/2007 | Reinl et al. .................. 435/6 |

FOREIGN PATENT DOCUMENTS

DE    32 46 079    6/1984

OTHER PUBLICATIONS

Rudikoff et al (1982. Proc Natl Acad Sci USA. 79: 1979-83).*
Singh et al (2003. Journal of Immunology. 171: 1401-1406).*
Kuhne et al. 2007. Journal of Immunology. 178: 131; 2 pages as printed.*
Suzuki et al (2007. Pathology International. 57: 413-420).*
Queen et al, 1989. PNAS. 86: 10029-10033.*
Riechmann et al, 1988. Nature. 332: 323-327.*
Singh, Udai P. et al, Inhibition of IFN-γ-Inducible Protein-10 Abrogates Colitis in IL-10$^{-/-}$ Mice, The Journal of Immunology, vol. 171, pp. 1401-1406 (2003).

* cited by examiner

*Primary Examiner* — Bridget E Bunner
*Assistant Examiner* — Zachary C Howard

(57) ABSTRACT

The present invention is directed to high affinity anti-human IP-10 antibodies or antigen-binding fragments of these antibodies, including chimeric, humanized or fully human antibodies. The present invention is also directed to a method of reducing the severity of at least one symptom of an inflammatory bowel disease in a subject in need thereof comprising administering to said subject an effective amount of an antagonist of IP-10, including the antibodies or antibody fragments of the present invention.

12 Claims, 2 Drawing Sheets

VH

```
                                               CDR1        40
HuAIP12    EVQLVQSGAE  VKKPGATVKI  SCKVSGYTFT  DYSMHWVRQA   SEQ ID NO. 45
HuAIP13    EVQLVQSGAE  VKKPGATVKI  SCKVSGYTFT  DYSMHWVRQA   SEQ ID NO. 13
T55I       EVQLVQSGAE  VKKPGATVKI  SCKVSGYTFT  DYSMHWVRQA   SEQ ID NO. 78
G104A      EVQLVQSGAE  VKKPGATVKI  SCKVSGYTFT  DYSMHWVRQA   SEQ ID NO. 79

CDR2                   80
HuAIP12    PGKGLKWMGW  INTETGEPTY  ADDFKGRFTF  TLDTSTSTAY
HuAIP13    PGKGLKWMGW  INTEIGEPTY  ADDFKGRFTF  TLDTSTSTAY

T55I       PGKGLKWMGW  INTEIGEPTY  ADDFKGRFTF  TLDTSTSTAY

G104A      PGKGLKWMGW  INTETGEPTY  ADDFKGRFTF  TLDTSTSTAY

CDR3         119
HuAIP12    MELSSLRSED  TAVYYCARNY  DYDGYFDVWG  QGTTVTVSS
HuAIP13    MELSSLRSED  TAVYYCARNY  DYDAYFDVWG  QGTTVTVSS
T55I       MELSSLRSED  TAVYYCARNY  DYDGYFDVWG  QGTTVTVSS
G104A      MELSSLRSED  TAVYYCARNY  DYDAYFDVWG  QGTTVTVSS
```

Alignment of the VH (A) and VL (B) amino acid sequences of HuAIP12, its derivatives (in A), and HuAIP13. The amino acid sequences of the mature VH and VL regions are shown in single letter code. Amino acids that differ from the counterparts in the HuAIP12 VH or VL are bold and double-underlined.

```
                                        CDR1          40
HuAIP12    DIQMTQSPSS  LSASVGDRVT  ITCKASQDIN  KYIAWYQQKP   SEQ ID NO. 46
HuAIP13    DIQMTQSPSS  LSASVGDRVT  ITCKADQDIN  KYIAWYQQKP   SEQ ID NO. 15

CDR2                      80
HuAIP12    GKAPKLLIHY  TSTLQPGIPS  RFSGSGSGRD  YTFTISSLQP
HuAIP13    GKAPKLLLHH  TSTLQPGIPS  RFSGSGSGRD  YTFTISSLQP

CDR3            107
HuAIP12    EDIATYYCLQ  YDNLLFTFGQ  GTKLEIK
HuAIP13    EDIATYYCLQ  YDSLLFTFGQ  GTKLEIK
```

Alignment of the VH (A) and VL (B) amino acid sequences of HuAIP12, its derivatives (in A), and HuAIP13. The amino acid sequences of the mature VH and VL regions are shown in single letter code. Amino acids that differ from the counterparts in the HuAIP12 VH or VL are bold and double-underlined.

FIGURE 1B

SEQUENCE LISTING

```
<160> NUMBER OF SEQ ID NOS: 79

<210> SEQ ID NO 1
<211> LENGTH: 98
<212> TYPE: PRT
<213> ORGANISM: Homo sapiens

<400> SEQUENCE: 1

Met Asn Gln Thr Ala Ile Leu Ile Cys Cys Leu Ile Phe Leu Thr Leu
1               5                   10                  15

Ser Gly Ile Gln Gly Val Pro Leu Ser Arg Thr Val Arg Cys Thr Cys
            20                  25                  30

Ile Ser Ile Ser Asn Gln Pro Val Asn Pro Arg Ser Leu Glu Lys Leu
        35                  40                  45

Glu Ile Ile Pro Ala Ser Gln Phe Cys Pro Arg Val Glu Ile Ile Ala
    50                  55                  60

Thr Met Lys Lys Lys Gly Glu Lys Arg Cys Leu Asn Pro Glu Ser Lys
65                  70                  75                  80

Ala Ile Lys Asn Leu Leu Lys Ala Val Ser Lys Glu Arg Ser Lys Arg
                85                  90                  95

Ser Pro

<210> SEQ ID NO 2
<211> LENGTH: 98
<212> TYPE: PRT
<213> ORGANISM: Homo sapiens

<400> SEQUENCE: 2

Met Asn Gln Thr Ala Ile Leu Ile Cys Cys Leu Ile Phe Leu Thr Leu
1               5                   10                  15

Ser Gly Ile Gln Gly Val Pro Leu Ser Arg Thr Val Arg Cys Thr Cys
            20                  25                  30

Ile Ser Ile Ser Asn Gln Pro Val Asn Pro Arg Ser Leu Glu Lys Leu
        35                  40                  45

Glu Ile Ile Pro Ala Ser Gln Phe Cys Pro Arg Val Glu Ile Ile Ala
    50                  55                  60

Thr Met Lys Lys Lys Gly Glu Lys Arg Cys Leu Asn Pro Glu Ser Lys
65                  70                  75                  80

Ala Ile Lys Asn Leu Leu Lys Ala Val Ser Lys Glu Arg Ser Lys Arg
                85                  90                  95
```

Ser Pro

<210> SEQ ID NO 3
<211> LENGTH: 119
<212> TYPE: PRT
<213> ORGANISM: Mus sp.

<400> SEQUENCE: 3

```
Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Met His Trp Val Lys Gln Ala Pro Gly Lys Gly Leu Lys Trp Met
        35                  40                  45

Gly Trp Ile Asn Thr Glu Ile Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Asn Tyr Asp Tyr Asp Ala Tyr Phe Asp Val Trp Gly Ala Gly
            100                 105                 110

Thr Thr Val Thr Val Ser Ser
        115
```

<210> SEQ ID NO 4
<211> LENGTH: 107
<212> TYPE: PRT
<213> ORGANISM: Mus sp.

<400> SEQUENCE: 4

```
Asp Ile Gln Met Thr Gln Ser Pro Ser Ser Leu Ser Ala Ser Leu Gly
1               5                   10                  15

Gly Lys Val Thr Ile Thr Cys Lys Ala Asp Gln Asp Ile Asn Lys Tyr
            20                  25                  30

Ile Ala Trp Tyr Gln His Lys Pro Gly Arg Gly Pro Arg Leu Leu Leu
        35                  40                  45

His His Thr Ser Thr Leu Gln Pro Gly Ile Pro Ser Arg Phe Ser Gly
    50                  55                  60

Ser Gly Ser Gly Arg Asp Tyr Ser Phe Ser Ile Ser Asn Leu Glu Pro
65                  70                  75                  80

Ala Asp Ile Ala Thr Tyr Tyr Cys Leu Gln Tyr Asp Ser Leu Leu Phe
                85                  90                  95

Thr Phe Gly Ser Gly Thr Lys Leu Glu Ile Lys
            100                 105
```

<210> SEQ ID NO 5
<211> LENGTH: 5
<212> TYPE: PRT
<213> ORGANISM: Mus sp.

<400> SEQUENCE: 5

```
Asp Tyr Ser Met His
1               5
```

<210> SEQ ID NO 6
<211> LENGTH: 17
<212> TYPE: PRT
<213> ORGANISM: Mus sp.

```
<400> SEQUENCE: 6

Trp Ile Asn Thr Glu Ile Gly Glu Pro Thr Tyr Ala Asp Asp Phe Lys
1               5                   10                  15
Gly

<210> SEQ ID NO 7
<211> LENGTH: 10
<212> TYPE: PRT
<213> ORGANISM: Mus sp.

<400> SEQUENCE: 7

Asn Tyr Asp Tyr Asp Ala Tyr Phe Asp Val
1               5                   10

<210> SEQ ID NO 8
<211> LENGTH: 11
<212> TYPE: PRT
<213> ORGANISM: Mus sp.

<400> SEQUENCE: 8

Lys Ala Asp Gln Asp Ile Asn Lys Tyr Ile Ala
1               5                   10

<210> SEQ ID NO 9
<211> LENGTH: 7
<212> TYPE: PRT
<213> ORGANISM: Mus sp.

<400> SEQUENCE: 9

His Thr Ser Thr Leu Gln Pro
1               5

<210> SEQ ID NO 10
<211> LENGTH: 9
<212> TYPE: PRT
<213> ORGANISM: Mus sp.

<400> SEQUENCE: 10

Leu Gln Tyr Asp Ser Leu Leu Phe Thr
1               5

<210> SEQ ID NO 11
<211> LENGTH: 414
<212> TYPE: DNA
<213> ORGANISM: Mus sp.

<400> SEQUENCE: 11
atggcttggg tgtggacctt gctattcctg atggcagctg cccaaagtat ccaagcacag     60
atccagttgg tgcagtctgg acctgagctg aagaagcctg agagacagt caagatctcc    120 tgcaaggctt ctggttatac cttcacagac tattcaatgc actgggtgaa gcaggctcca    180
ggaaagggtt taaagtggat gggctggata aacactgaga ttggtgagcc aacatatgca    240
gatgacttca aggacggtt tgccttctct ttggaaacct ctgccagcac tgcctatttg    300
cagatcaaca acctcaaaaa tgaggacacg gctacatatt tctgtgctag aaactatgat    360
tacgacgcgt acttcgatgt ctggggcgca gggaccacgg tcaccgtctc ctca          414

<210> SEQ ID NO 12
<211> LENGTH: 381
<212> TYPE: DNA
<213> ORGANISM: Mus sp.
```

-continued

<400> SEQUENCE: 12

```
atgagaccgt ctattcagtt cctggggctc ttgttgttct ggcttcatgg tgctcagtgt      60
gacatccaga tgacacagtc tccatcctca ctgtctgcat ctctgggagg caaagtcacc     120
atcacttgca aggcagacca agacattaac aagtatatag cttggtacca acacaagcct     180
ggaagaggtc ctaggctgct cctacatcac acatctacat tacagccagg catcccatca     240
aggttcagtg aagtgggtc tgggagagat tattccttca gcatcagcaa cctggagcct     300
gcagatattg caacttatta ttgtctacag tatgatagtc ttctattcac gttcggctcg     360
gggacaaagt tggaaataaa a                                               381
```

<210> SEQ ID NO 13
<211> LENGTH: 119
<212> TYPE: PRT
<213> ORGANISM: Homo sapiens

<400> SEQUENCE: 13

```
Glu Val Gln Leu Val Gln Ser Gly Ala Glu Val Lys Lys Pro Gly Ala
  1               5                  10                  15

Thr Val Lys Ile Ser Cys Lys Val Ser Gly Tyr Thr Phe Thr Asp Tyr
             20                  25                  30

Ser Met His Trp Val Arg Gln Ala Pro Gly Lys Gly Leu Lys Trp Met
         35                  40                  45

Gly Trp Ile Asn Thr Glu Ile Gly Glu Pro Thr Tyr Ala Asp Asp Phe
     50                  55                  60

Lys Gly Arg Phe Thr Phe Thr Leu Asp Thr Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asn Tyr Asp Tyr Asp Ala Tyr Phe Asp Val Trp Gly Gln Gly
            100                 105                 110

Thr Thr Val Thr Val Ser Ser
        115
```

<210> SEQ ID NO 14
<211> LENGTH: 87
<212> TYPE: PRT
<213> ORGANISM: Homo sapiens

<400> SEQUENCE: 14

```
Glu Val Gln Leu Val Gln Ser Gly Ala Glu Val Lys Lys Pro Gly Ala
  1               5                  10                  15

Thr Val Lys Ile Ser Cys Lys Val Ser Gly Tyr Thr Phe Thr Trp Val
             20                  25                  30

Gln Gln Ala Pro Gly Lys Gly Leu Glu Trp Met Gly Arg Val Thr Ile
         35                  40                  45

Thr Ala Asp Thr Ser Thr Asp Thr Ala Tyr Met Glu Leu Ser Ser Leu
     50                  55                  60

Arg Ser Glu Asp Thr Ala Val Tyr Tyr Cys Ala Thr Trp Gly Gln Gly
 65                  70                  75                  80

Thr Thr Val Thr Val Ser Ser
                 85
```

<210> SEQ ID NO 15
<211> LENGTH: 107
<212> TYPE: PRT
<213> ORGANISM: Homo sapiens

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Lys Ala Asp Gln Asp Ile Asn Lys Tyr
            20                  25                  30

Ile Ala Trp Tyr Gln Gln Lys Pro Gly Lys Ala Pro Lys Leu Leu Leu
        35                  40                  45

His His Thr Ser Thr Leu Gln Pro Gly Ile Pro Ser Arg Phe Ser Gly
    50                  55                  60

Ser Gly Ser Gly Arg Asp Tyr Thr Phe Thr Ile Ser Ser Leu Gln Pro
65                  70                  75                  80

Glu Asp Ile Ala Thr Tyr Tyr Cys Leu Gln Tyr Asp Ser Leu Leu Phe
                85                  90                  95

Thr Phe Gly Gln Gly Thr Lys Leu Glu Ile Lys
            100                 105

<210> SEQ ID NO 16
<211> LENGTH: 80
<212> TYPE: PRT
<213> ORGANISM: Homo sapiens

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Trp Tyr Gln Gln Lys Pro Gly Lys Ala
            20                  25                  30

Pro Lys Leu Leu Ile Tyr Gly Val Pro Ser Arg Phe Ser Gly Ser Gly
        35                  40                  45

Ser Gly Thr Asp Phe Thr Phe Thr Ile Ser Ser Leu Gln Pro Glu Asp
    50                  55                  60

Ile Ala Thr Tyr Tyr Cys Phe Gly Gln Gly Thr Lys Leu Glu Ile Lys
65                  70                  75                  80

<210> SEQ ID NO 17
<211> LENGTH: 412
<212> TYPE: DNA
<213> ORGANISM: Homo sapiens

<400> SEQUENCE: 17
acgcgtccac catgagaccg tctattcagt tcctggggct cttgttgttc tggcttcatg    60
gtgctcagtg tgacatccag atgacacagt ctccatcctc actgtctgca tctgtgggag   120
acagagtcac catcacttgc aaggcagacc aagacattaa caagtatata gcttggtacc   180
aacagaagcc tggaaaggct cctaagctgc tcctacatca cacatctaca ttacagccag   240
gcatcccatc aaggttcagt ggaagtgggt ctggaagaga ttataccttc accatcagca   300
gcctgcagcc tgaagatatt gcaacttatt attgtctaca gtatgatagt cttctattca   360
cgttcggcca ggggacaaag ttggaaataa aacgtaagta cttttttcta ga            412

<210> SEQ ID NO 18
<211> LENGTH: 127
<212> TYPE: PRT
<213> ORGANISM: Homo sapiens

<400> SEQUENCE: 18

Met Arg Pro Ser Ile Gln Phe Leu Gly Leu Leu Leu Phe Trp Leu His
1               5                   10                  15

Gly Ala Gln Cys Asp Ile Gln Met Thr Gln Ser Pro Ser Ser Leu Ser

```
                    20                  25                  30
Ala Ser Val Gly Asp Arg Val Thr Ile Thr Cys Lys Ala Asp Gln Asp
        35                  40                  45

Ile Asn Lys Tyr Ile Ala Trp Tyr Gln Gln Lys Pro Gly Lys Ala Pro
 50                  55                  60

Lys Leu Leu His His Thr Ser Thr Leu Gln Pro Gly Ile Pro Ser
65                   70                  75                  80

Arg Phe Ser Gly Ser Gly Ser Gly Arg Asp Tyr Thr Phe Thr Ile Ser
                85                  90                  95

Ser Leu Gln Pro Glu Asp Ile Ala Thr Tyr Tyr Cys Leu Gln Tyr Asp
            100                 105                 110

Ser Leu Leu Phe Thr Phe Gly Gln Gly Thr Lys Leu Glu Ile Lys
            115                 120                 125

<210> SEQ ID NO 19
<211> LENGTH: 446
<212> TYPE: DNA
<213> ORGANISM: Homo sapiens

<400> SEQUENCE: 19
acgcgtccac catggactcg aggttgaact tggtattcct ggtgctaatt ctcaaaggtg     60
tccaatgtga ggtccagttg gtgcagtctg gagctgaggt gaagaagcct ggagcgacag    120
tcaagatctc ctgcaaagtg tctggttata ccttcacaga ctattcaatg cactgggtta    180
ggcaggctcc aggaaagggt ctaaagtgga tgggctggat aaacactgag attggtgagc    240
caacatatgc agatgacttc aagggacggt ttaccttcac tttggacacc tctaccagca    300
ctgcctatat ggagctcagc agcctccgaa gtgaggacac ggctgtatat tactgtgcta    360
gaaactatga ttacgatgcg tacttcgatg tctggggcca agggaccaca gtcaccgtct    420
cctcaggtaa gaatggccac tctaga                                         446

<210> SEQ ID NO 20
<211> LENGTH: 138
<212> TYPE: PRT
<213> ORGANISM: Homo sapiens

<400> SEQUENCE: 20

Met Asp Ser Arg Leu Asn Leu Val Phe Leu Val Leu Ile Leu Lys Gly
 1               5                  10                  15

Val Gln Cys Glu Val Gln Leu Val Gln Ser Gly Ala Glu Val Lys Lys
            20                  25                  30

Pro Gly Ala Thr Val Lys Ile Ser Cys Lys Val Ser Gly Tyr Thr Phe
        35                  40                  45

Thr Asp Tyr Ser Met His Trp Val Arg Gln Ala Pro Gly Lys Gly Leu
 50                  55                  60

Lys Trp Met Gly Trp Ile Asn Thr Glu Ile Gly Glu Pro Thr Tyr Ala
65                   70                  75                  80

Asp Asp Phe Lys Gly Arg Phe Thr Phe Thr Leu Asp Thr Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Asn Tyr Asp Tyr Asp Ala Tyr Phe Asp Val Trp
            115                 120                 125

Gly Gln Gly Thr Thr Val Thr Val Ser Ser
            130                 135
```

<210> SEQ ID NO 21
<211> LENGTH: 75
<212> TYPE: DNA
<213> ORGANISM: Artificial sequence
<220> FEATURE:
<223> OTHER INFORMATION: Description of Artificial Sequence: Synthetic
      primer

<400> SEQUENCE: 21
tataacgcgt ccaccatgga ctcgaggttg aacttggtat tcctggtgct aattctcaaa    60
ggtgtccaat gtgag                                                     75

<210> SEQ ID NO 22
<211> LENGTH: 72
<212> TYPE: DNA
<213> ORGANISM: Artificial sequence
<220> FEATURE:
<223> OTHER INFORMATION: Description of Artificial Sequence: Synthetic
      primer

<400> SEQUENCE: 22
gactgtcgct ccaggcttct tcacctcagc tccagactgc accaactgga cctcacattg    60
gacacctttg ag                                                        72

<210> SEQ ID NO 23
<211> LENGTH: 74
<212> TYPE: DNA
<213> ORGANISM: Artificial sequence
<220> FEATURE:
<223> OTHER INFORMATION: Description of Artificial Sequence: Synthetic
      primer

<400> SEQUENCE: 23
agaagcctgg agcgacagtc aagatctcct gcaaagtgtc tggttatacc ttcacagact    60
attcaatgca ctgg                                                      74

<210> SEQ ID NO 24
<211> LENGTH: 72
<212> TYPE: DNA
<213> ORGANISM: Artificial sequence
<220> FEATURE:
<223> OTHER INFORMATION: Description of Artificial Sequence: Synthetic
      primer

<400> SEQUENCE: 24
gtgtttatcc agcccatcca ctttagaccc tttcctggag cctgcctaac ccagtgcatt    60
gaatagtctg tg                                                        72

<210> SEQ ID NO 25
<211> LENGTH: 74
<212> TYPE: DNA
<213> ORGANISM: Artificial sequence
<220> FEATURE:
<223> OTHER INFORMATION: Description of Artificial Sequence: Synthetic
      primer

<400> SEQUENCE: 25
tggatgggct ggataaacac tgagattggt gagccaacat atgcagatga cttcaaggga    60
cggtttacct tcac                                                      74

<210> SEQ ID NO 26
<211> LENGTH: 78
<212> TYPE: DNA
<213> ORGANISM: Artificial sequence
<220> FEATURE:

```
<223> OTHER INFORMATION: Description of Artificial Sequence: Synthetic
      primer

<400> SEQUENCE: 26
tcctcacttc ggaggctgct gagctccata taggcagtgc tggtagaggt gtccaaagtg    60
aaggtaaacc gtcccttg                                                  78

<210> SEQ ID NO 27
<211> LENGTH: 78
<212> TYPE: DNA
<213> ORGANISM: Artificial sequence
<220> FEATURE:
<223> OTHER INFORMATION: Description of Artificial Sequence: Synthetic
      primer

<400> SEQUENCE: 27
cagcagcctc cgaagtgagg acacggctgt atattactgt gctagaaact atgattacga    60
tgcgtacttc gatgtctg                                                  78

<210> SEQ ID NO 28
<211> LENGTH: 77
<212> TYPE: DNA
<213> ORGANISM: Artificial sequence
<220> FEATURE:
<223> OTHER INFORMATION: Description of Artificial Sequence: Synthetic
      primer

<400> SEQUENCE: 28
tatatctaga gtggccattc ttacctgagg agacggtgac tgtggtccct tggccccaga    60
catcgaagta cgcatcg                                                   77

<210> SEQ ID NO 29
<211> LENGTH: 24
<212> TYPE: DNA
<213> ORGANISM: Artificial sequence
<220> FEATURE:
<223> OTHER INFORMATION: Description of Artificial Sequence: Synthetic
      primer

<400> SEQUENCE: 29
tataacgcgt ccaccatgga ctcg                                           24

<210> SEQ ID NO 30
<211> LENGTH: 24
<212> TYPE: DNA
<213> ORGANISM: Artificial sequence
<220> FEATURE:
<223> OTHER INFORMATION: Description of Artificial Sequence: Synthetic
      primer

<400> SEQUENCE: 30
tatatctaga gtggccattc ttac                                           24

<210> SEQ ID NO 31
<211> LENGTH: 72
<212> TYPE: DNA
<213> ORGANISM: Artificial sequence
<220> FEATURE:
<223> OTHER INFORMATION: Description of Artificial Sequence: Synthetic
      primer

<400> SEQUENCE: 31
tataacgcgt ccaccatgag accgtctatt cagttcctgg ggctcttgtt gttctggctt    60
catggtgctc ag                                                        72
```

```
<210> SEQ ID NO 32
<211> LENGTH: 75
<212> TYPE: DNA
<213> ORGANISM: Artificial sequence
<220> FEATURE:
<223> OTHER INFORMATION: Description of Artificial Sequence: Synthetic
      primer

<400> SEQUENCE: 32
tctcccacag atgcagacag tgaggatgga gactgtgtca tctggatgtc acactgagca      60
ccatgaagcc agaac                                                      75

<210> SEQ ID NO 33
<211> LENGTH: 71
<212> TYPE: DNA
<213> ORGANISM: Artificial sequence
<220> FEATURE:
<223> OTHER INFORMATION: Description of Artificial Sequence: Synthetic
      primer

<400> SEQUENCE: 33
ctgtctgcat ctgtgggaga cagagtcacc atcacttgca aggcagacca agacattaac      60
aagtatatag c                                                          71

<210> SEQ ID NO 34
<211> LENGTH: 72
<212> TYPE: DNA
<213> ORGANISM: Artificial sequence
<220> FEATURE:
<223> OTHER INFORMATION: Description of Artificial Sequence: Synthetic
      primer

<400> SEQUENCE: 34
tgatgtagga gcagcttagg agcctttcca ggcttctgtt ggtaccaagc tatatacttg      60
ttaatgtctt gg                                                         72

<210> SEQ ID NO 35
<211> LENGTH: 68
<212> TYPE: DNA
<213> ORGANISM: Artificial sequence
<220> FEATURE:
<223> OTHER INFORMATION: Description of Artificial Sequence: Synthetic
      primer

<400> SEQUENCE: 35
tcctaagctg ctcctacatc acacatctac attacagcca ggcatccat caaggttcag       60 tggaagtg                                                              68

<210> SEQ ID NO 36
<211> LENGTH: 62
<212> TYPE: DNA
<213> ORGANISM: Artificial sequence
<220> FEATURE:
<223> OTHER INFORMATION: Description of Artificial Sequence: Synthetic
      primer

<400> SEQUENCE: 36
tgcaggctgc tgatggtgaa ggtataatct cttccagacc cacttccact gaaccttgat      60
gg                                                                    62

<210> SEQ ID NO 37
<211> LENGTH: 76
<212> TYPE: DNA
<213> ORGANISM: Artificial sequence
```

```
<220> FEATURE:
<223> OTHER INFORMATION: Description of Artificial Sequence: Synthetic
      primer

<400> SEQUENCE: 37
cttcaccatc agcagcctgc agcctgaaga tattgcaact tattattgtc tacagtatga      60
tagtcttcta ttcacg                                                     76

<210> SEQ ID NO 38
<211> LENGTH: 78
<212> TYPE: DNA
<213> ORGANISM: Artificial sequence
<220> FEATURE:
<223> OTHER INFORMATION: Description of Artificial Sequence: Synthetic
      primer

<400> SEQUENCE: 38
tatatctaga aaaagtact tacgttttat ttccaacttt gtccctggc cgaacgtgaa        60 tagaagacta tcatactg                                                   78

<210> SEQ ID NO 39
<211> LENGTH: 24
<212> TYPE: DNA
<213> ORGANISM: Artificial sequence
<220> FEATURE:
<223> OTHER INFORMATION: Description of Artificial Sequence: Synthetic
      primer

<400> SEQUENCE: 39
tataacgcgt ccaccatgag accg                                            24

<210> SEQ ID NO 40
<211> LENGTH: 24
<212> TYPE: DNA
<213> ORGANISM: Artificial sequence
<220> FEATURE:
<223> OTHER INFORMATION: Description of Artificial Sequence: Synthetic
      primer

<400> SEQUENCE: 40
tatatctaga aaaagtact tacg                                             24

<210> SEQ ID NO 41
<211> LENGTH: 119
<212> TYPE: PRT
<213> ORGANISM: Mus sp.

<400> SEQUENCE: 41

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Asp Tyr
            20                  25                  30

Ser Met His Trp Val Lys Gln Ala Pro Gly Lys Gly Leu Lys Trp Met
        35                  40                  45

Gly Trp Ile Asn Thr Glu Thr Gly Glu Pro Thr Tyr Ala Asp Asp Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Asn Tyr Asp Tyr Asp Gly Tyr Phe Asp Val Trp Gly Ala Gly
            100                 105                 110
```

```
Thr Thr Val Thr Val Ser Ser
        115

<210> SEQ ID NO 42
<211> LENGTH: 107
<212> TYPE: PRT
<213> ORGANISM: Mus sp.

<400> SEQUENCE: 42

Asp Ile Gln Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Lys Tyr
            20                  25                  30

Ile Ala Trp Tyr Gln His Lys Pro Gly Lys Gly Pro Arg Leu Leu Ile
        35                  40                  45

His Tyr Thr Ser Thr Leu Gln Pro Gly Ile Pro Ser Arg Phe Ser Gly
    50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Asp Asn Leu Leu Phe
                85                  90                  95

Thr Phe Gly Ser Gly Thr Lys Leu Glu Ile Lys
            100                 105

<210> SEQ ID NO 43
<211> LENGTH: 414
<212> TYPE: DNA
<213> ORGANISM: Mus sp.

<400> SEQUENCE: 43
atggcttggg tgtggacctt gctattcctg atggcagctg cccaaagtat ccaagcacag    60
atccagttgg tgcagtctgg acctgagctg aagaagcctg agagacagt caagatctcc    120 tgcaaggctt ctggttatac cttcacagac tattcaatgc actgggtgaa gcaggctcca    180
ggaaagggtt taaagtggat gggctggata aacactgaga ctggtgagcc aacatatgca    240
gatgacttca agggacggtt tgccttctct ttggaaacct ctgccagcac tgcctatttg    300
cagatcaaca acctcaaaaa tgaggacacg gctacatatt tctgtgctag aaactatgat    360
tacgacgggg acttcgatgt ctggggcgca gggaccacgg tcaccgtctc ctca          414

<210> SEQ ID NO 44
<211> LENGTH: 381
<212> TYPE: DNA
<213> ORGANISM: Mus sp.

<400> SEQUENCE: 44
atgagaccgt ctattcagtt cctggggctc ttgttgttct ggcttcatgg tgctcagtgt    60
gacatccaga tgacacagtc tccatcctca ctgtctgcat ctctgggagg caaagtcacc    120
atcacttgca aggcaagcca agacattaac aagtatatag cttggtacca acacaagcct    180
ggaaaaggtc ctaggctgct catacattac acatctacat acagccagg catcccatca    240 aggttcagtg aagtgggtc tgggagagat tattccttca gcatcagcaa cctggagcct    300
gaagatattg caacttatta ttgtctacag tatgataatc ttctattcac gttcggctcg    360
gggacaaagt tggaaataaa a                                              381

<210> SEQ ID NO 45
<211> LENGTH: 119
<212> TYPE: PRT
```

<213> ORGANISM: Homo sapiens

<400> SEQUENCE: 45

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Tyr
            20                  25                  30

Ser Met His Trp Val Arg Gln Ala Pro Gly Lys Gly Leu Lys Trp Met
        35                  40                  45

Gly Trp Ile Asn Thr Glu Thr Gly Glu Pro Tyr Ala Asp Asp Phe
    50                  55                  60

Lys Gly Arg Phe Thr Phe Thr Leu Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Tyr Asp Tyr Asp Gly Tyr Phe Asp Val Trp Gly Gln Gly
            100                 105                 110

Thr Thr Val Thr Val Ser Ser
        115

<210> SEQ ID NO 46
<211> LENGTH: 107
<212> TYPE: PRT
<213> ORGANISM: Homo sapiens

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Lys Tyr
            20                  25                  30

Ile Ala Trp Tyr Gln Gln Lys Pro Gly Lys Ala Pro Lys Leu Leu Ile
        35                  40                  45

His Tyr Thr Ser Thr Leu Gln Pro Gly Ile Pro Ser Arg Phe Ser Gly
    50                  55                  60

Ser Gly Ser Gly Arg Asp Tyr Thr Phe Thr Ile Ser Ser Leu Gln Pro
65                  70                  75                  80

Glu Asp Ile Ala Thr Tyr Tyr Cys Leu Gln Tyr Asp Asn Leu Leu Phe
                85                  90                  95

Thr Phe Gly Gln Gly Thr Lys Leu Glu Ile Lys
            100                 105

<210> SEQ ID NO 47
<211> LENGTH: 412
<212> TYPE: DNA
<213> ORGANISM: Homo sapiens

<400> SEQUENCE: 47

```
acgcgtccac catgagaccg tctattcagt tcctggggct cttgttgttc tggcttcatg      60
gtgctcagtg tgacatccag atgacacagt ctccatcctc actgtctgca tctgtgggag     120
acagagtcac catcacttgc aaggcaagcc aagacattaa caagtatata gcttggtacc     180
aacagaagcc tggaaaggct cctaagctgc tcatacatta cacatctaca ttacagccag     240
gcatcccatc aaggttcagt ggaagtgggt ctggaagaga ttatacctcc accatcagca     300
gcctgcagcc tgaagatatt gcaacttatt attgtctaca gtatgataat cttctattca     360
cgttcggcca ggggacaaag ttggaaataa aacgtaagta cttttttcta ga            412
```

<210> SEQ ID NO 48
<211> LENGTH: 127
<212> TYPE: PRT
<213> ORGANISM: Homo sapiens

<400> SEQUENCE: 48

```
Met Arg Pro Ser Ile Gln Phe Leu Gly Leu Leu Leu Phe Trp Leu His
1               5                   10                  15

Gly Ala Gln Cys Asp Ile Gln Met Thr Gln Ser Pro Ser Ser Leu Ser
            20                  25                  30

Ala Ser Val Gly Asp Arg Val Thr Ile Thr Cys Lys Ala Ser Gln Asp
        35                  40                  45

Ile Asn Lys Tyr Ile Ala Trp Tyr Gln Gln Lys Pro Gly Lys Ala Pro
    50                  55                  60

Lys Leu Leu Ile His Tyr Thr Ser Thr Leu Gln Pro Gly Ile Pro Ser
65                  70                  75                  80

Arg Phe Ser Gly Ser Gly Ser Gly Arg Asp Tyr Thr Phe Thr Ile Ser
                85                  90                  95

Ser Leu Gln Pro Glu Asp Ile Ala Thr Tyr Tyr Cys Leu Gln Tyr Asp
            100                 105                 110

Asn Leu Leu Phe Thr Phe Gly Gln Gly Thr Lys Leu Glu Ile Lys
        115                 120                 125
```

<210> SEQ ID NO 49
<211> LENGTH: 446
<212> TYPE: DNA
<213> ORGANISM: Homo sapiens

<400> SEQUENCE: 49

```
acgcgtccac catggactcg aggttgaact tggtattcct ggtgctaatt ctcaaaggtg    60
tccaatgtga ggtccagttg gtgcagtctg gagctgaggt gaagaagcct ggagcgacag   120
tcaagatctc ctgcaaagtg tctggttata ccttcacaga ctattcaatg cactgggtta   180
ggcaggctcc aggaaagggt ctaaagtgga tgggctggat aaacactgag actggtgagc   240
caacatatgc agatgacttc aagggacggt ttaccttcac tttggacacc tctaccagca   300
ctgcctatat ggagctcagc agcctccgat ccgaggacac ggctgtatat tactgtgcta   360
gaaactatga ttacgatggg tacttcgatg tctggggcca agggaccaca gtcaccgtct   420
cctcaggtaa gaatggccac tctaga                                        446
```

<210> SEQ ID NO 50
<211> LENGTH: 138
<212> TYPE: PRT
<213> ORGANISM: Homo sapiens

<400> SEQUENCE: 50

```
Met Asp Ser Arg Leu Asn Leu Val Phe Leu Val Leu Ile Leu Lys Gly
1               5                   10                  15

Val Gln Cys Glu Val Gln Leu Val Gln Ser Gly Ala Glu Val Lys Lys
            20                  25                  30

Pro Gly Ala Thr Val Lys Ile Ser Cys Lys Val Ser Gly Tyr Thr Phe
        35                  40                  45

Thr Asp Tyr Ser Met His Trp Val Arg Gln Ala Pro Gly Lys Gly Leu
    50                  55                  60

Lys Trp Met Gly Trp Ile Asn Thr Glu Thr Gly Glu Pro Thr Tyr Ala
65                  70                  75                  80

Asp Asp Phe Lys Gly Arg Phe Thr Phe Thr Leu Asp Thr Ser Thr Ser
                85                  90                  95
```

Thr Ala Tyr Met Glu Leu Ser Ser Leu Arg Ser Glu Asp Thr Ala Val
            100                 105                 110

Tyr Tyr Cys Ala Arg Asn Tyr Asp Tyr Asp Gly Tyr Phe Asp Val Trp
            115                 120                 125

Gly Gln Gly Thr Thr Val Thr Val Ser Ser
            130                 135

<210> SEQ ID NO 51
<211> LENGTH: 75
<212> TYPE: DNA
<213> ORGANISM: Artificial sequence
<220> FEATURE:
<223> OTHER INFORMATION: Description of Artificial Sequence: Synthetic
      primer

<400> SEQUENCE: 51
tataacgcgt ccaccatgga ctcgaggttg aacttggtat tcctggtgct aattctcaaa    60
ggtgtccaat gtgag                                                    75

<210> SEQ ID NO 52
<211> LENGTH: 72
<212> TYPE: DNA
<213> ORGANISM: Artificial sequence
<220> FEATURE:
<223> OTHER INFORMATION: Description of Artificial Sequence: Synthetic
      primer

<400> SEQUENCE: 52
gactgtcgct ccaggcttct tcacctcagc tccagactgc accaactgga cctcacattg    60
gacacctttg ag                                                       72

<210> SEQ ID NO 53
<211> LENGTH: 74
<212> TYPE: DNA
<213> ORGANISM: Artificial sequence
<220> FEATURE:
<223> OTHER INFORMATION: Description of Artificial Sequence: Synthetic
      primer

<400> SEQUENCE: 53
agaagcctgg agcgacagtc aagatctcct gcaaagtgtc tggttatacc ttcacagact    60
attcaatgca ctgg                                                     74

<210> SEQ ID NO 54
<211> LENGTH: 72
<212> TYPE: DNA
<213> ORGANISM: Artificial sequence
<220> FEATURE:
<223> OTHER INFORMATION: Description of Artificial Sequence: Synthetic
      primer

<400> SEQUENCE: 54
gtgtttatcc agcccatcca ctttagaccc tttcctggag cctgcctaac ccagtgcatt    60
gaatagtctg tg                                                       72

<210> SEQ ID NO 55
<211> LENGTH: 74
<212> TYPE: DNA
<213> ORGANISM: Artificial sequence
<220> FEATURE:
<223> OTHER INFORMATION: Description of Artificial Sequence: Synthetic
      primer

<400> SEQUENCE: 55

```
tggatgggct ggataaacac tgagactggt gagccaacat atgcagatga cttcaaggga      60
cggtttacct tcac                                                       74

<210> SEQ ID NO 56
<211> LENGTH: 78
<212> TYPE: DNA
<213> ORGANISM: Artificial sequence
<220> FEATURE:
<223> OTHER INFORMATION: Description of Artificial Sequence: Synthetic
      primer

<400> SEQUENCE: 56
tcctcggatc ggaggctgct gagctccata taggcagtgc tggtagaggt gtccaaagtg      60
aaggtaaacc gtcccttg                                                   78

<210> SEQ ID NO 57
<211> LENGTH: 78
<212> TYPE: DNA
<213> ORGANISM: Artificial sequence
<220> FEATURE:
<223> OTHER INFORMATION: Description of Artificial Sequence: Synthetic
      primer

<400> SEQUENCE: 57
cagcagcctc cgatccgagg acacggctgt atattactgt gctagaaact atgattacga      60
tgggtacttc gatgtctg                                                   78

<210> SEQ ID NO 58
<211> LENGTH: 77
<212> TYPE: DNA
<213> ORGANISM: Artificial sequence
<220> FEATURE:
<223> OTHER INFORMATION: Description of Artificial Sequence: Synthetic
      primer

<400> SEQUENCE: 58
tatatctaga gtggccattc ttacctgagg agacggtgac tgtggtccct tggccccaga     60
catcgaagta cccatcg                                                    77

<210> SEQ ID NO 59
<211> LENGTH: 24
<212> TYPE: DNA
<213> ORGANISM: Artificial sequence
<220> FEATURE:
<223> OTHER INFORMATION: Description of Artificial Sequence: Synthetic
      primer

<400> SEQUENCE: 59
tataacgcgt ccaccatgga ctcg                                            24

<210> SEQ ID NO 60
<211> LENGTH: 24
<212> TYPE: DNA
<213> ORGANISM: Artificial sequence
<220> FEATURE:
<223> OTHER INFORMATION: Description of Artificial Sequence: Synthetic
      primer

<400> SEQUENCE: 60
tatatctaga gtggccattc ttac                                            24

<210> SEQ ID NO 61
<211> LENGTH: 72
<212> TYPE: DNA
```

```
<213> ORGANISM: Artificial sequence
<220> FEATURE:
<223> OTHER INFORMATION: Description of Artificial Sequence: Synthetic
      primer

<400> SEQUENCE: 61
tataacgcgt ccaccatgag accgtctatt cagttcctgg ggctcttgtt gttctggctt     60
catggtgctc ag                                                        72

<210> SEQ ID NO 62
<211> LENGTH: 75
<212> TYPE: DNA
<213> ORGANISM: Artificial sequence
<220> FEATURE:
<223> OTHER INFORMATION: Description of Artificial Sequence: Synthetic
      primer

<400> SEQUENCE: 62
tctcccacag atgcagacag tgaggatgga gactgtgtca tctggatgtc acactgagca     60
ccatgaagcc agaac                                                     75

<210> SEQ ID NO 63
<211> LENGTH: 71
<212> TYPE: DNA
<213> ORGANISM: Artificial sequence
<220> FEATURE:
<223> OTHER INFORMATION: Description of Artificial Sequence: Synthetic
      primer

<400> SEQUENCE: 63
ctgtctgcat ctgtgggaga cagagtcacc atcacttgca aggcaagcca agacattaac     60
aagtatatag c                                                         71

<210> SEQ ID NO 64
<211> LENGTH: 72
<212> TYPE: DNA
<213> ORGANISM: Artificial sequence
<220> FEATURE:
<223> OTHER INFORMATION: Description of Artificial Sequence: Synthetic
      primer

<400> SEQUENCE: 64
taatgtatga gcagcttagg agcctttcca ggcttctgtt ggtaccaagc tatatacttg     60
ttaatgtctt gg                                                        72

<210> SEQ ID NO 65
<211> LENGTH: 68
<212> TYPE: DNA
<213> ORGANISM: Artificial sequence
<220> FEATURE:
<223> OTHER INFORMATION: Description of Artificial Sequence: Synthetic
      primer

<400> SEQUENCE: 65
tcctaagctg ctcatacatt acacatctac attacagcca ggcatcccat caaggttcag     60
tggaagtg                                                             68

<210> SEQ ID NO 66
<211> LENGTH: 62
<212> TYPE: DNA
<213> ORGANISM: Artificial sequence
<220> FEATURE:
<223> OTHER INFORMATION: Description of Artificial Sequence: Synthetic
      primer
```

```
<400> SEQUENCE: 66
tgcaggctgc tgatggtgaa ggtataatct cttccagacc cacttccact gaaccttgat    60
gg                                                                   62

<210> SEQ ID NO 67
<211> LENGTH: 76
<212> TYPE: DNA
<213> ORGANISM: Artificial sequence
<220> FEATURE:
<223> OTHER INFORMATION: Description of Artificial Sequence: Synthetic
      primer

<400> SEQUENCE: 67
cttcaccatc agcagcctgc agcctgaaga tattgcaact tattattgtc tacagtatga    60
taatcttcta ttcacg                                                    76

<210> SEQ ID NO 68
<211> LENGTH: 78
<212> TYPE: DNA
<213> ORGANISM: Artificial sequence
<220> FEATURE:
<223> OTHER INFORMATION: Description of Artificial Sequence: Synthetic
      primer

<400> SEQUENCE: 68
tatatctaga aaaaagtact tacgtttat ttccaactttt gtccctggc cgaacgtgaa    60 tagaagatta tcatactg                                                  78

<210> SEQ ID NO 69
<211> LENGTH: 24
<212> TYPE: DNA
<213> ORGANISM: Artificial sequence
<220> FEATURE:
<223> OTHER INFORMATION: Description of Artificial Sequence: Synthetic
      primer

<400> SEQUENCE: 69
tataacgcgt ccaccatgag accg                                           24

<210> SEQ ID NO 70
<211> LENGTH: 24
<212> TYPE: DNA
<213> ORGANISM: Artificial sequence
<220> FEATURE:
<223> OTHER INFORMATION: Description of Artificial Sequence: Synthetic
      primer

<400> SEQUENCE: 70
tatatctaga aaaaagtact tacg                                           24

<210> SEQ ID NO 71
<211> LENGTH: 20
<212> TYPE: DNA
<213> ORGANISM: Artificial sequence
<220> FEATURE:
<223> OTHER INFORMATION: Description of Artificial Sequence: Synthetic
      primer

<400> SEQUENCE: 71
gccagtggat agactgatgg                                                20

<210> SEQ ID NO 72
<211> LENGTH: 21
<212> TYPE: DNA
<213> ORGANISM: Artificial sequence
```

-continued

```
<220> FEATURE:
<223> OTHER INFORMATION: Description of Artificial Sequence: Synthetic
      primer

<400> SEQUENCE: 72
gatggataca gttggtgcag c                                              21

<210> SEQ ID NO 73
<211> LENGTH: 17
<212> TYPE: PRT
<213> ORGANISM: Homo sapiens

<400> SEQUENCE: 73

Trp Ile Asn Thr Glu Thr Gly Glu Pro Thr Tyr Ala Asp Asp Phe Lys
1               5                   10                  15
Gly

<210> SEQ ID NO 74
<211> LENGTH: 10
<212> TYPE: PRT
<213> ORGANISM: Homo sapiens

<400> SEQUENCE: 74

Asn Tyr Asp Tyr Asp Gly Tyr Phe Asp Val
1               5                   10

<210> SEQ ID NO 75
<211> LENGTH: 11
<212> TYPE: PRT
<213> ORGANISM: Homo sapiens

<400> SEQUENCE: 75

Lys Ala Ser Gln Asp Ile Asn Lys Tyr Ile Ala
1               5                   10

<210> SEQ ID NO 76
<211> LENGTH: 7
<212> TYPE: PRT
<213> ORGANISM: Homo sapiens

<400> SEQUENCE: 76

Tyr Thr Ser Thr Leu Gln Pro
1               5

<210> SEQ ID NO 77
<211> LENGTH: 9
<212> TYPE: PRT
<213> ORGANISM: Homo sapiens

<400> SEQUENCE: 77

Leu Gln Tyr Asp Asn Leu Leu Phe Thr
1               5

<210> SEQ ID NO 78
<211> LENGTH: 119
<212> TYPE: PRT
<213> ORGANISM: Homo sapiens

<400> SEQUENCE: 78

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Tyr
            20                  25                  30

Ser Met His Trp Val Arg Gln Ala Pro Gly Lys Gly Leu Lys Trp Met
```

-continued

```
                35                  40                  45
Gly Trp Ile Asn Thr Glu Ile Gly Glu Pro Thr Tyr Ala Asp Asp Phe
        50                  55                  60

Lys Gly Arg Phe Thr Phe Thr Leu Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Tyr Asp Tyr Asp Gly Tyr Phe Asp Val Trp Gly Gln Gly
                100                 105                 110

Thr Thr Val Thr Val Ser Ser
        115

<210> SEQ ID NO 79
<211> LENGTH: 119
<212> TYPE: PRT
<213> ORGANISM: Homo sapiens

<400> SEQUENCE: 79

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Tyr
                20                  25                  30

Ser Met His Trp Val Arg Gln Ala Pro Gly Lys Gly Leu Lys Trp Met
            35                  40                  45

Gly Trp Ile Asn Thr Glu Thr Gly Glu Pro Thr Tyr Ala Asp Asp Phe
        50                  55                  60

Lys Gly Arg Phe Thr Phe Thr Leu Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Tyr Asp Tyr Asp Ala Tyr Phe Asp Val Trp Gly Gln Gly
                100                 105                 110

Thr Thr Val Thr Val Ser Ser
        115
```

TREATMENT OF INFLAMMATORY BOWEL DISEASES WITH ANTI-IP-10 ANTIBODIES

PRIORITY CLAIM

This is the §371 U.S. National Stage of International Application No. PCT/US2004/037600, filed on Nov. 10, 2004, which in turn claims the benefit of U.S. Provisional Application No. 60/527,882, filed on Dec. 4, 2003, which is incorporated herein by reference in its entirety.

FIELD OF THE INVENTION

The present invention applies to the technical fields of immunology and disease treatment. In particular, it concerns high affinity antibodies against human IP-10 and methods of using these antibodies for the treatment of inflammatory bowel diseases.

BACKGROUND OF THE INVENTION

The burgeoning family of chemo-attractant cytokines, also known as chemokines, comprises the most diverse and largest subset of cytokines identified to date. Chemokines are characterized by their capacity to induce the directional migration and activation of leukocytes, as well as other somatic cell types, and thus play major roles in acute and chronic inflammation (William, P. et al., Fundamental Immunology, 4$^{th}$ Edition, Lippincott-Raven pp. 791-794 (1990)).

Chemokines also promote humoral and cell-mediated immune reactions; regulate cell adhesion, angiogenesis, leukocyte trafficking, and homing; and contribute to lymphopoiesis and hematopoiesis. Chemokines are produced by a wide variety of leukocytes and other cell types in response to irritants, polyclonal stimulants, antigens, and endogenous cytokines. A variety of chemokines have been detected at local inflammatory sites in a great number of disease states. Chemokines play a central role in host defense against infectious organisms, including HIV-1. Furthermore, chemokines participate in the pathogenesis of diverse conditions such as reperfusion injuries including strokes, acute respiratory distress syndrome (ARDS), immune complex-induced glomerulonephritis, atherosclerosis, and autoimmune reactions (William, P. et al., Fundamental Immunology, 4$^{th}$ Edition, Lippincott-Raven pp. 791-794 (1990)).

IP-10 (CXCL10) is a chemokine that is induced by interferon γ and is the ligand for CXCR3. CXCR3 is expressed on human activated/memory T cells (Qin et al., J. Clin. Invest. 101:746 (1998)). Over-expression of IP-10 at the site of inflammation potently attracts CDCR3+ activated T cells and antibody secreting plasma cells. In human patient samples, elevated levels of IP-10 have been found in a number of autoimmune diseases, including multiple sclerosis (MS) (Balashov et al., Proc. Natl. Acad. Sci USA 96:6873 (1999)); Sorensen et al., J. Neuroimmunol. 127:59 (2002)), rheumatoid arthritis (RA) (Patel et al., Clin. Immunol 98:39 (2001)), systemic lupus erythematosis (Narumi et al., Euro. J. Immunol. 32:1784 (2002)), Type-I diabetes (Nicolette et al., Dialectologies 45:1107 (2002)), Graves' disease (Romagnani et al., Am. J. Patrol. 161:195 (2002)), psoriasis (Flier, 2002; Gottlieb et al., J. Exp. Med. 168:941 (1998)), and autoimmune liver disease (Nishioji et al, Clin. Exp. Immunol. 123: 271 (2001)). Animal model studies have also demonstrated that IP-10 may play a role in multiple sclerosis (MS), rheumatoid arthritis (RA), and airway hyperactivity and inflammation. U.S. Pat. No. 6,184,358 discloses the antibodies to and nucleic acids encoding CXCR3 (this and all other U.S. patents and patent applications cited herein are hereby incorporated herein in their entirety). PCT Publication No. WO 02/15932 is directed to a method of preventing demyelination in a subject by administering to a subject a neutralizing agent specific for IP-10.

There have been reports that elevated IP-10 levels have been detected in human IBD. Grimm, M., et al. reported detecting elevated IP-10 levels in formalin-fixed colon resections from Crohn's disease (hereinafter, "CD") patients as compared to colon resections from non-inflamed (but cancer bearing) colons by in situ hybridization (Inflammatory Bowel Dis. 2:88-96 (1996)). Uguccioni, M., et al. reported detecting elevated IP-10 expression in endoscopic biopsies from ulcerative colitis (hereinafter, "UC") patients as compared to biopsies from normal colons by immunohistochemistry (Amer. J. Pathol. 155:331-6 (1999)). However, the above-referenced publications have not examined the therapeutic potential of anti-IP-10 antibodies in inflammatory bowel diseases (hereinafter, "IBD"). As IP-10 is induced by both IFN-γ and TNF-α, an antibody targeting this chemokine would be expected to operate downstream of both of these cytokines in the inflammatory pathway, and thus could be a more specific intervention and exhibit fewer or less severe side effects, as compared with the existing approaches for treating IBD. The present invention provides for potent neutralizing anti-IP-10 antibodies comprising the disclosed amino acid sequences and the methods of using an antagonist of IP-10 for the treatment of IBD, including CD and UC.

SUMMARY OF THE INVENTION

The present invention is also directed to an antibody or an antigen-binding fragment thereof, wherein said antibody comprises a variable heavy chain amino acid sequence of SEQ ID NO. 45 and a variable light chain amino acid sequence of SEQ ID NO. 46, designated herein as HuAIP12.

The present invention is also directed to a method of reducing severity of at least one symptom of inflammatory bowel disease in a subject in need thereof comprising administering to said subject an effective amount of an antibody or an antigen-binding fragment thereof comprising a variable heavy chain amino acid sequence of SEQ ID NO. 45 and a variable light chain amino acid sequence of SEQ ID NO. 46.

The present invention is also directed to a pharmaceutical composition comprising an antibody or an antigen-binding fragment thereof comprising a variable heavy chain amino acid sequence of SEQ ID NO. 45 and a variable light chain amino acid sequence of SEQ ID NO. 46.

The present invention is also directed to an antibody or an antigen-binding fragment thereof, wherein said antibody comprises a variable heavy chain amino acid sequence of SEQ ID NO:78 and a variable light chain amino acid sequence of SEQ ID NO.46, designated herein as the HuAIP12 T55 I variant.

The present invention is also directed to a method of reducing severity of at least one symptom of inflammatory bowel disease in a subject in need thereof comprising administering to said subject an effective amount of an antibody or an antigen-binding fragment thereof comprising a variable heavy chain amino acid sequence of SEQ ID NO. 78 and a variable light chain amino acid sequence of SEQ ID NO. 46.

The present invention is also directed to a pharmaceutical composition comprising an antibody or an antigen-binding fragment thereof comprising a variable heavy chain amino acid sequence of SEQ ID NO. 78 and a variable light chain amino acid sequence of SEQ ID NO. 46.

The present invention is also directed to a method of reducing severity of at least one symptom of inflammatory bowel disease in a subject in need thereof comprising administering to said subject an effective amount of an antibody or an antigen-binding fragment thereof comprising a variable heavy chain amino acid sequence of SEQ ID NO. 78 and a variable light chain amino acid sequence of SEQ ID NO.48.

The present invention is also directed to a pharmaceutical composition comprising an antibody or an antigen-binding fragment thereof comprising a variable heavy chain amino acid sequence of SEQ ID NO. 78 and a variable light chain amino acid sequence of SEQ ID NO. 48.

BRIEF DESCRIPTION OF THE DRAWINGS

FIG. 1A depicts the HuAIP12 VH amino acid sequence (SEQ ID NO. 45), the HuAIP13 VH amino acid sequence (SEQ ID NO. 13), the HuAIP12 T55I variant VH amino acid sequence (SEQ ID NO. 78) and the HuAIP12 G104A variant VH amino acid sequence (SEQ ID NO. 79).

FIG. 1B depicts the HuAIP12 VL amino acid sequence (SEQ ID NO. 46) and the HuAIP13 VL amino acid sequence (SEQ ID NO. 15).

DETAILED DESCRIPTION OF THE PREFERRED EMBODIMENTS

Figure 2:
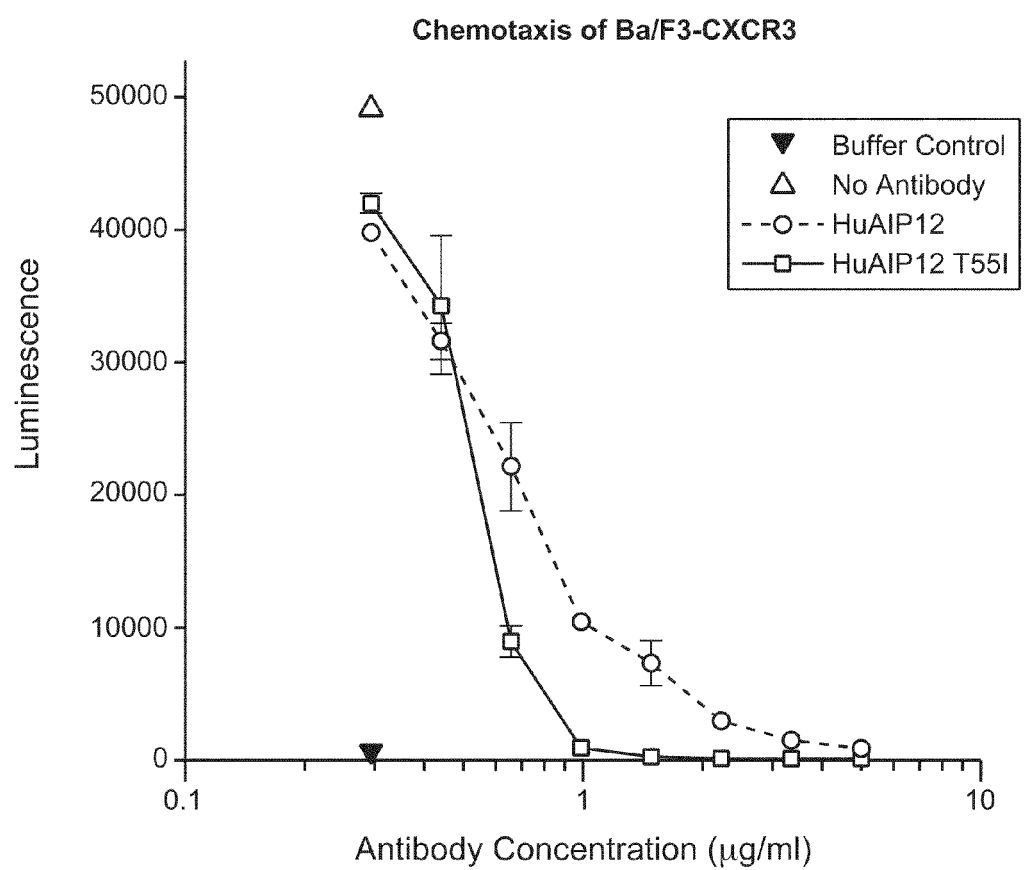
FIG. 2 depicts the inhibition of IP-10 mediated chemotaxis of BA/F3-CXCR3 cells by the HuAIP12 T55I variant antibody as compared to the original, unmodified HuAIP12 antibody.

Definitions:

As used herein, the term "antibody" or "immunoglobulin" refers to a protein consisting of one or more polypeptides substantially encoded by immunoglobulin genes. The recognized immunoglobulin genes include the kappa, lambda, alpha, gamma (IgG$_1$, IgG$_2$, IgG$_3$, IgG$_4$), delta, epsilon and mu constant region genes, as well as the myriad immunoglobulin variable V region genes (as indicated below, there are V genes for both H-heavy- and L-light-chains). Full-length immunoglobulin "light chains" (about 25 Kd or 214 amino acids) are encoded by a variable region gene, V-kappa or V-lambda, at the NH2-terminus (about 110 amino acids) and, respectively, a kappa or lambda constant region gene at the COOH-terminus. Full-length immunoglobulin "heavy chains" (about 50 Kd or 446 amino acids), are similarly encoded by a variable region gene (about 116 amino acids) and one of the other aforementioned constant region genes, e.g., gamma (encoding about 330 amino acids).

One form of immunoglobulin constitutes the basic structural unit of an antibody. This form is a tetramer and consists of two identical pairs of immunoglobulin chains, each pair having one light and one heavy chain. In each pair, the light and heavy chain variable regions are together responsible for binding to an antigen, and the constant regions are responsible for the antibody effector functions. In addition to the tetrameric antibodies, immunoglobulins may exist in a variety of other forms including, for example, Fv, Fab, and (Fab')$_2$, as well as bifunctional hybrid antibodies (e.g., Lanzavecchia et al., Eur. J. Immunol. 17, 105 (1987)) and in single chains (e.g., Huston et al., Proc. Natl. Acad. Sci. U.S.A., 85, 5879-5883 (1988) and Bird et al., Science, 242, 423-426 (1988), which are incorporated herein by reference). (See, generally, Hood et al., "Immunology", Benjamin, N.Y., 2nd ed. (1984), and Hunkapiller and Hood, Nature, 323, 15-16 (1986), which are incorporated herein by reference).

The term "humanized antibody" or "humanized immunoglobulin" refers to an immunoglobulin comprising a human framework, at least one and preferably all complementarity determining regions (CDRs) from a non-human antibody, and in which any constant region present is substantially identical to a human immunoglobulin constant region, i.e., at least about 85-90%, preferably at least 95% identical. Hence, all parts of a humanized immunoglobulin, except possibly the CDRs, are substantially identical to corresponding parts of one or more native human immunoglobulin sequences. See, e.g. Queen et al., U.S. Pat. Nos. 5,5301,101; 5,585,089; 5,693,762; and 6,180,370 (each of which is incorporated by reference in its entirety).

The term "chimeric antibody" refers to an antibody in which the constant region comes from an antibody of one species (typically human) and the variable region comes from an antibody of another species (typically rodent).

By "an effective" amount of an antagonist, an antibody, a drug or pharmacologically active agent or pharmaceutical formulation is meant a sufficient amount of the antagonist, antibody, drug, agent or formulation to provide the desired effect.

A "subject," or "patient" is used interchangeably herein, and refers to a vertebrate, preferably a mammal, more preferably a human.

The term "differentially expressed" means that a polypeptide or a mRNA encoding such a polypeptide is expressed in a type of cells or tissues that are in a diseased stage at a higher level than in the same type of cells that are in a non-diseased stage, for example, 30% more, 50% more, 100% more, 200% more, 300% more, or 400% more. For instance, if IP-10 is differentially expressed in diseased colon tissue of a patient suffering from an inflammatory bowel disease, the protein or mRNA of IP-10 will express at a higher level in the diseased colon cells of such a patient compared to the normal colon cells of the same patient. The protein expression level can be measured by the standard technology known in the art, such as western blot, ELISA, immunohistological staining, or FACS analysis. The mRNA expression level can be measured by the standard technology known in the art, such as, Real Time PCR, RT-PCR, Northern blot, RNA protection assay, in situ hybridization, or Taqman® expression assay.

The term "epitope" refers to any portion (determinant) of a protein that is capable of eliciting an immune response and being specifically bound by an antibody. Epitope determinants usually consist of active surface groupings of molecules such as amino acids or GAG side chains and usually have specific three-dimensional structural characteristics, as well as specific charge characteristics. Two antibodies are said to bind to substantially the same epitope of a protein if amino acid mutations in the protein that reduce or eliminate binding of one antibody also reduce or eliminate binding of the other antibody, and/or if the antibodies compete for binding to the protein, i.e., binding of one antibody to the protein reduces or eliminates binding of the other antibody. The determination of whether two antibodies bind substantially to the same epitope is accomplished by the methods known in the art, such as a competition assay. In conducting an antibody competition study between a control antibody (for example, one of the anti-IP-10 antibodies described herein) and any test antibody, one may first label the control antibody with a detectable label, such as biotin, enzymatic, radioactive label or fluorescence label, to enable the subsequent identification. An antibody that binds to substantially the same epitope as the control antibody should be able to compete for binding and thus should reduce the control antibody binding, as evidenced by a reduction in the bound label.

The term "derived from" means "obtained from" or "produced by" or "descending from".

I. Antagonists

The antagonists of IP-10 include any molecules that directly or indirectly counteract, reduce, or inhibit IP-10 biological activities. In a preferred embodiment, the antagonists of IP-10 compete with or even block the binding of IP-10 to their receptors, such as CXCR3. The antagonists should counteract, reduce, or inhibit the chemoattractive activities of IP-10, for example, the recruitment of lymphocytes to the inflammatory sites.

In a preferred aspect, the antagonists directly interact with IP-10. Preferably, the antagonists are polypeptides. More preferably, the polypeptides bind to IP-10, and even more preferably, the antagonists are antibodies or antibody fragments that bind to IP-10 and inhibit at least one biological activity of IP-10.

The antagonists can also be any polypeptides or peptides that inhibit IP-10 activities but do not directly interact with IP-10. In one aspect, these antagonists block the binding of IP-10 to its receptors such as CXCR3. For example, the antagonists can be mutated IP-10 molecules, such as dominant-negative mutants derived from a wild-type IP-10 by terminal truncations or amino acid substitutions. Preferably such mutated IP-10 molecules retain the binding ability to the signaling molecules of IP-10 but lose the ability of triggering the downstream signaling transduction of IP-10. Therefore, the mutated IP-10 molecules can compete with the wild-type IP-10 and thus block the activities of the wild-type IP-10. The terminal truncations and amino acid substitutions can be made by the standard mutagenesis and molecular cloning techniques. The mutated IP-10 molecules can be administered into the target cells by standard delivery means known in the art, such as, lipid or viral transfections.

In another aspect, the antagonists interact with and regulate the up-stream or down-stream components of the IP-10 signaling pathway and indirectly reduce or enhance the activities of IP-10. It is known that IP-10 activities are induced by interferon γ and act through receptors which belong to a superfamily of seven transmembrane spanning G-protein coupled receptors (Murphy, P. M., Annu. Rev. Immunol., 12: 593-633 (1994); Gerard, C. and N. P. Gerard, Curr. Opin. Immunol., 6:140-145 (1994)). This family of G-protein coupled (serpentine) receptors comprises a large group of integral membrane proteins, containing seven transmembrane-spanning regions. The receptors are coupled to G proteins, which are heterotrimeric regulatory proteins capable of binding GTP and mediating signal transduction from coupled receptors, for example, by the production of intracellular mediators. Accordingly, any molecules capable of regulating this pathway can be candidate antagonists, including, but not limited to, G-protein antagonists known in the art. Yeast two-hybrid and variant screens offer preferred methods for identifying endogenous additional IP-10 interacting proteins (Finley, R. L. et al. in Cloning-Expression Systems: A Practical Approach, eds. Glover, D. & Hames, B. D. (Oxford University Press, Oxford, England), pp. 169-203 (1996); Fashema, S. F. et al., Gene 250: 1-14 (2000); Drees, B. L., CUK Opin Chem Biol 3: 64-70 (1999); Vidal, M. and Legrain, P. Nucleic Acids. Res. 27:9191-29 (1999); and U.S. Pat. No. 5,928,868). Mass spectrometry is an alternative method for the elucidation of protein complexes (reviewed in, e. g., Pandley, A. and Mann, M., Nature 405: 837-846 (2000); Yates, J. R. 3rd, Trends Genet. 16: 5-8 (2000)).

Alternatively, the antagonists can inhibit the mRNA and/or protein expression of IP-10. The IP-10 expression can be regulated at the level of transcription, such as by regulators of transcription factors of IP-10, or at the level of mRNA splicing, or at translation or post-translation level.

The antagonists can also be nucleic acids, including, but not limited to, antisense nucleic acids of the nucleic acid sequence encoding part or full of IP-10 or having substantial sequence similarity of IP-10. The sequence of IP-10 is known in the art and is disclosed herein. Subsequently, anti-sense nucleic acid probes of DNA of IP-10, and the optimal conditions of the anti-sense blocking can be developed by using the related techniques known to a skilled artisan in the field of molecular biology. Similarly, the nucleic acid reagent may belong to the class of short interfering RNA or siRNA.

The antagonists of the present invention also include small molecules, which often modulate the functions of proteins with enzymatic functions and/or proteins containing protein interaction domains. Chemical agents, referred to in the art as "small molecule" compounds are typically organic, non-peptide molecules, having a molecular weight less than 10,000, preferably less than 5,000, more preferably less than 1,000, and most preferably less than 500 daltons. This class of antagonists includes chemically synthesized molecules, for instance, compounds from combinatorial chemical libraries. Synthetic compounds may be rationally designed or identified based on known or inferred properties of the IP-10 protein or may be identified by screening compound libraries. Alternative appropriate antagonists of this class are natural products, particularly secondary metabolites from organisms such as plants or fungi, which can also be identified by screening compound libraries for IP-10-modulating activities. Methods for generating and obtaining compounds are well known in the art (Schreiber, S. L., Science 151: 1964-1969 (2000); Radmann, J. and Gunther, J., Science 151: 1947-1948 (2000)). Additionally, candidate clinical compounds are generated with specific regard to clinical and pharmacological properties. For example, the reagents may be derivatized and re-screened using in vitro and i* vivo assays to optimize activity and minimize toxicity for pharmaceutical development.

II. Antibodies

The antibodies against IP-10 of the present invention may be polyclonal or monoclonal and should bind to at least one epitope of IP-10 derived from any species, such as human, rat, mouse, chicken, rabbit, preferably a human IP-10. The antibodies should bind to a) a wild-type full-length IP-10 protein, or b) a functionally active fragment or derivative thereof The amino acid sequence of the full-length wild-type human IP-10 is presented in SEQ ID NO: 1 (MNQTAILICC LIFLTLSGIQ GVPLSRTVRC TCISISNQPV NPRSLEKLEI IPASQFCPRV EIIATMKKKG EKRCLNPESK AIKNLLKAVS KERSKRSP). A "functionally active" IP-10 fragment or derivative exhibits one or more functional activities associated with the full-length, wild-type IP-10 protein, such as antigenic or immunogenic activity, ability to bind natural cellular substrates, such as its cognate receptor, etc. The functional activity of IP-10 proteins, derivatives and fragments can be assayed by various methods known to one skilled in the art (Coligan et al., eds., Current Protocols in Protein Science, John Wiley & Sons, Inc., Somerset, N.J. (1998)). For purposes herein, functionally active fragments also include those fragments that comprise one or more structural domains of an IP-10 polypeptide, such as a binding domain. Protein domains can be identified using the PFAM program (Bateman A., et al., Nucleic Acids Res. 27: 260-2 (1999).

IP-10 polypeptide derivatives typically share a certain degree of sequence identity or sequence similarity with SEQ ID NO: 1 or a fragment thereof. IP-10 derivatives can be produced by various methods known in the art. The manipulations that result in their production can occur at the gene or protein level. For example, a cloned IP-10 gene sequence can be cleaved at appropriate sites with restriction endonuclease(s) (Wells et al., Philos. Trans. R. Sot. London SerA 317: 415 (1986)) followed by further enzymatic modification, if desired, then isolated, and ligated in vitro, and expressed to produce the desired derivative. Alternatively, an IP-10 gene can be mutated in vitro or in vivo to create and/or destroy translation, initiation, and/or termination sequences, or to create variations in coding regions and/or to form new restriction endonuclease sites or destroy preexisting ones, to facilitate further in vitro modification. A variety of mutagenesis techniques are known in the art such as chemical mutagenesis, in vitro site-directed mutagenesis (Carter et al., Nucl. Acids Res. 13: 4331 (1986)), use of TAB® linkers (available from Pharmacia and Upjohn, Kalamazoo, Mich.), etc.

The anti-IP-10 antibodies of the present invention include antibodies having any type of constant region, including IgM, IgG, IgD, IgA and IgE, and any isotype, including IgG1, IgG2a, IgG2b, IgG3 and IgG4. The light chains of the antibodies can either be kappa light chains or lambda light chains.

In a preferred aspect, anti-IP antibodies preferably bind to an IP-10 epitope at a binding affinity of at least $10^6 M^{-1}$, $10^7 M^{-1}$, $10^8 M^{-1}$, $10^9 M^{-1}$, or $10^{10} M^{-1}$.

In another preferred aspect, the antibodies of the present invention neutralize at least one biological activity of IP-10, such as receptor binding activities, signaling transductions, and cellular responses induced by IP-10. These neutralizing antibodies are capable of competing with the binding of IP-10 to its receptors, such as CXCR3, or even block the binding completely. These antibodies should inhibit or completely neutralize signaling activities, and/or induction of cellular responses, for example, calcium influx or chemotaxis of lymphocytes.

In a preferred embodiment, the antibodies are capable of inhibiting the interactions between IP-10 and CXCR3 and/or IP-10 mediated chemotaxis activities. Preferably, a concentration of 0.005, 0.01, 0.05, 0.1, 0.25, 0.5, 1, 2, 5, 10, or 100 μg/ml of the antibodies will block at least 10%, 25%, 50%, 90%, 95%, 99% or essentially 100% of the binding of IP-10 to CXCR3 or IP-10-mediated chemotaxis, especially when the IP-10 is also used at one of these concentrations or at a molar concentration that is 0.005, 0.01, 0.05, 0.1, 0.25, 0.5, or 1.0 of the concentration of the antibody.

Exemplary neutralizing antibodies were generated and are the monoclonal antibodies referred to as: AIP13, AIP12, AIP8, AIP14, and AIP21 ("AIP" numbers refer to different anti-IP10 antibodies generated at PDL). An exemplary neutralizing humanized antibody is the monoclonal antibody HuAIP13. Almost all of them inhibit, or even completely block the IP-10-mediated chemotaxis. AIP13 and AIP12 have the most potent neutralizing capability. As little as 1.3 μg/ml of AIP13 or 1.6 μg/ml of AIP12 inhibit IP-10-mediated chemotaxis by about 50%.

The amino acid sequences of the mature heavy chain variable region and the mature light chain variable region of AIP13 are depicted in SEQ ID NOs: 3 and 4, respectively. The amino acid sequences of the mature heavy chain variable region and the mature light chain variable region of HuAIP13 are depicted in SEQ ID NOs: 13 and 15, respectively. SEQ ID NOs: 5, 6, and 7 depict the AIP13 and HuAIP13 amino acid sequences of the heavy chain CDR1 (DYSMH), CDR2 (WINTEIGEPTYADDFKG), and CDR3 (NYDYDAYFDV), respectively. SEQ ID NOs: 8, 9, and 10 depict the AIP13 and HuAIP13 amino acid sequences of the light chain CDR1 (KADQDINKYIA), CDR2 (HTSTLQP), and CDR3 (LQYDSLLFT), respectively.

The amino acid sequences of the mature heavy chain variable region and the mature light chain variable region of AIP12 are depicted in SEQ ID NOs: 41 and 42, respectively. The amino acid sequences of the mature heavy chain variable region and the mature light chain variable region of HuAIP12 are depicted in SEQ ID NOs: 45 and 46, respectively. SEQ ID NOs: 5, 73, and 74 depict the amino acid sequences of the heavy chain CDR1 (DYSMH), CDR2 (WINTETGEPTYADDFKG), and CDR3 (NYDYDGYFDV), respectively. SEQ ID NOs: 75, 76, and 77 depict the amino acid sequences of the light chain CDR1 (KASQDINKYIA), CDR2 (YTSTLQP), and CDR3 (LQYDNLLFT), respectively.

The present invention includes the analogs of the antibodies or antibody fragments described herein. These analogs should retain the antigen-binding utility. Preferred analogs include a) the CDRs comprising an amino acid sequences sharing at least 60%, 80% or 90-95% amino acid sequence identity with SEQ ID NOs: 5, 6, 7, 8, 9, or 10; b) the CDRs comprising an amino acid sequences sharing at least 60%, 80% or 90-95% amino acid sequence identity with SEQ ID NOs: 5, 73, 74, 75, 76, or 77; c) a mature heavy chain variable region comprising an amino acid sequences sharing at least 60%, 80% or 90-95% amino acid sequence identity with SEQ ID NO: 3 or 13; and/or a mature light chain variable region comprising an amino acid sequences sharing at least 60%, 80% or 90-95% amino acid sequence identity with SEQ ID NO: 4 or 15; d) a mature heavy chain variable region comprising an amino acid sequence sharing at least 60%, 80% or 90-95% amino acid sequence identity with SEQ ID NO: 41 or 45; and/or a mature light chain variable region comprising an amino acid sequence sharing at least 60%, 80% or 90-95% amino acid sequence identity with SEQ ID NO: 42 or 46; and e) antibodies or antibody fragments comprising these heavy chain and/or light chain variable regions. More preferred analogs of exemplified antibodies differ from exemplified antibodies or antibody fragments by conservative amino acid substitutions. For the purpose of classifying amino acid substitutions as conservative or nonconservative, amino acids may be grouped as follows: Group I (hydrophobic sidechains): met, ala, val, leu, ile; Group II (neutral hydrophilic side chains): cys, ser, thr; Group III (acidic side chains): asp, glu; Group IV (basic side chains): asn, gln, his, lys, arg; Group V (residues influencing chain orientation): gly, pro; and Group VI (aromatic side chains): trp, tyr, phe. Conservative substitutions involve substitutions between amino acids in the same class. Non-conservative substitutions constitute exchanging a member of one of these classes for a member of another. The analogs of the present invention can be made by amino acid substitutions via mutagenesis methods known in the art.

The present invention provides for the polynucleotide molecules encoding the antibodies and antibody fragments and their analogs described herein. Because of the degeneracy of the genetic code, a variety of nucleic acid sequences encode each immunoglobulin amino acid sequence. The desired nucleic acid sequences can be produced by de novo solid-phase synthesis or by PCR mutagenesis of an earlier prepared variant of the desired polynucleotide. In a preferred embodiment, the codons that are used comprise those that are typical for human or mouse (see, e.g., Nakamura, Y., Nucleic Acids Res. 28: 292 (2000)). An exemplary polynucleotide sequence encoding the mature anti-IP-10 antibody heavy chain variable region of SEQ ID NO: 3 is provided in SEQ ID NO: 11. An exemplary polynucleotide sequence encoding the mature anti-IP-10 antibody light chain variable region of SEQ ID NO: 4 is provided in SEQ ID NO: 12. An exemplary polynucleotide sequence encoding the mature anti-IP-10 antibody heavy chain variable region of SEQ ID NO: 41 is provided in SEQ ID NO: 43. An exemplary polynucleotide sequence encoding the mature anti-IP-10 antibody light chain variable region of SEQ ID NO: 42 is provided in SEQ ID NO: 44.

Methods of determining percent identity are known in the art. "Percent (%) sequence identity" with respect to a specified subject sequence, or a specified portion thereof, may be defined as the percentage of nucleotides or amino acids in the candidate derivative sequence identical with the nucleotides or amino acids in the subject sequence (or specified portion thereof), after aligning the sequences and introducing gaps, if necessary to achieve the maximum percent sequence identity, as generated by the program WU-BLAST-2.0a19 (Altschul et al., J. Mol. Biol. 215:403-410 (1997);) with search parameters set to default values. The HSPS and HSPS2 parameters are dynamic values and are established by the program itself depending upon the composition of the particular sequence and composition of the particular database against which the sequence of interest is being searched. Any two antibody sequences can only be aligned in one way, by using the numbering scheme in Kabat (Kabat, E. et al., "Sequences of Proteins of Immunological Interest", U.S. Department of Health and Human Service (1983)). Therefore, for antibodies, percent identity has a unique and well-defined meaning. A "% identity value" is determined by the number of matching identical nucleotides or amino acids divided by the sequence length for which the percent identity is being reported.

The present invention includes the monoclonal antibodies that bind to substantially the same epitope as any one of these above-exemplified antibodies.

Antibodies against IP-10 of all species of origins are included in the present invention. Non-limiting exemplary natural antibodies include antibodies derived from human, chicken, goats, and rodents (e.g., rats, mice, hamsters and rabbits), including transgenic rodents genetically engineered to produce human antibodies (see, e.g., Lonberg et al., WO93/12227; U.S. Pat. No. 5,545,806; and Kucherlapati, et al., WO91/10741; U.S. Pat. No. 6,150,584, which are herein incorporated by reference in their entirety). Natural antibodies are the antibodies produced by a host animal. In a preferred embodiment, the antibody is an isolated antibody that binds to or neutralizes IP-10.

The monoclonal antibodies are produced by conventional hybridoma methodology known in the art, as described originally by Kohler and Milstein, Nature 256: 495-7 (1975); Eur. J. Immunol. 6: 511 (1976)). More experimental details of producing the monoclonal antibodies described herein are disclosed in the Examples.

The polyclonal forms of the anti-IP-10 antibodies are also included in the present invention. Preferably, these antibodies neutralize at least one activity of IP-10, or bind to the epitopes that the described monoclonal antibodies bind to in the present invention. The polyclonal antibody can be produced by immunization of host animals by IP-10 or the fragments thereof. The polyclonal antibodies are secreted into the bloodstream and can be recovered with known techniques. Purified forms of these antibodies can, of course, be readily prepared by standard purification techniques, preferably including affinity chromatography with Protein A, anti-immunoglobulin, or the antigen itself. In any case, in order to monitor the success of immunization, the antibody levels with respect to the antigen in serum will be monitored using standard techniques such as ELISA, RIA, and the like.

Recombinant antibodies against IP-10 are also included in the present invention. These recombinant antibodies have the same amino acid sequence as the natural antibodies or have altered amino acid sequences as compared with the natural antibodies in the present invention. They can be made in any expression systems including both prokaryotic and eukaryotic expression systems or using phage display methods (see, e.g., Dower et al., WO91/17271 and McCafferty et al., WO92/01047; U.S. Pat. No. 5,969,108, which are herein incorporated by reference in their entirety).

The genetically altered anti-IP-10 antibodies should be functionally equivalent to the above-mentioned natural antibodies and recombinant antibodies. Modified antibodies providing improved stability and/or therapeutic efficacy are preferred. Examples of modified antibodies include those with conservative substitutions of amino acid residues, and one or more deletions or additions of amino acids that do not significantly deleteriously alter the antigen binding utility. Substitutions can range from changing or modifying one or more amino acid residues to complete redesign of a region as long as the therapeutic utility is maintained. Antibodies of this invention can be modified post-translationally (e.g., acetylation, and phosphorylation) or can be modified synthetically (e.g., the attachment of a labeling group or cytotoxic agent). Preferred genetically altered antibodies are chimeric antibodies and humanized antibodies.

The chimeric antibody is an antibody having a variable region and a constant region derived from two different antibodies, typically derived from separate species. Preferably, the variable region of the chimeric antibody is derived from murine and the constant region is derived from human, so that the chimeric antibody has a longer half-life and is less immunogenic when administered to a human subject.

In one embodiment, the murine variable regions are derived from any one of the monoclonal antibodies described herein, including the non-limiting examples: a) the monoclonal antibodies comprising a mature heavy chain variable region comprising amino acid sequence of SEQ ID NO: 3 and/or a mature light chain variable region comprising amino acid sequence of SEQ ID NO: 4; b) the antibodies that substantially bind to the same epitope of any antibodies of a); or c) the analogs of any antibodies of a).

In another embodiment, the murine variable regions are derived from any one of the monoclonal antibodies described herein, including the non-limiting examples: a) the monoclonal antibodies comprising a mature heavy chain variable region comprising amino acid sequence of SEQ ID NO: 41 and/or a mature light chain variable region comprising amino acid sequence of SEQ ID NO: 42; b) the antibodies that substantially bind to the same epitope of any antibodies of a); or c) the analogs of any antibodies of a).

In order to produce the chimeric antibodies, the portions derived from two different species (e.g., human constant region and murine variable or binding region) can be joined together chemically by conventional techniques or can be prepared as single contiguous proteins with genetic engineering techniques. The molecules encoding the proteins of both the light chain and heavy chain portions of the chimeric antibody can be expressed as contiguous proteins. The method of making the chimeric antibody is disclosed in U.S. Pat. Nos. 5,677,427; 6,120,767; and 6,329,508, each of which is incorporated herein by reference in its entirety.

The genetically altered antibodies used in the present invention include humanized antibodies that bind to or neutralize IP-10. In one embodiment, said humanized antibody comprising CDRs of a mouse donor immunoglobulin and heavy chain and light chain frameworks of a human acceptor immunoglobulin. In one example, the humanized antibodies are the humanized versions of a) the monoclonal antibodies comprising a mature heavy chain variable region comprising amino acid sequence of SEQ ID NO: 3 and/or a mature light chain variable region comprising amino acid sequence of SEQ ID NO: 4; b) the antibodies that bind to the same epitope of any antibodies of a); or c) the analogs of any antibodies of a). In another example, the humanized antibodies are the humanized versions of a) the monoclonal antibodies comprising a mature heavy chain variable region comprising amino acid sequence of SEQ ID NO: 41 and/or a mature light chain variable region comprising amino acid sequence of SEQ ID NO: 42; b) the antibodies that bind to the same epitope of any antibodies of a); or c) the analogs of any antibodies of a). The method of making humanized antibody is disclosed in U.S. Pat. Nos: 5,530,101; 5,585,089; 5,693,761; 5,693,762; and 6,180,370, each of which is incorporated by reference in its entirety.

Anti-IP-10 fully human antibodies are also included in the present invention. In a preferred embodiment of the present invention, said fully human antibodies are isolated human antibodies and neutralize the activities of IP-10 described herein. HuAIP13 is an exemplification of humanized antibody that binds to IP-10. The amino acid sequences of the HuAIP13 heavy chain variable region and light chain variable region are SEQ ID No.:13 and 15, respectively. HuAIP12 is another exemplification of humanized antibody that binds to IP-10. The amino acid sequences of the HuAIP12 heavy chain variable region and light chain variable region are SEQ ID No.:45 and 46, respectively.

Fully human antibodies against IP-10 are produced by a variety of techniques. One example is trioma methodology. The basic approach and an exemplary cell fusion partner, SPAZ4, for use in this approach have been described by Oestberg et al., Hybridoma 2:361-367 (1983); Oestberg, U.S. Pat. No. 4,634,664; and Engleman et al., U.S. Pat. No. 4,634,666 (each of which is incorporated herein by reference in its entirety)

Human antibodies against IP-10 can also be produced from non-human transgenic animals having transgenes encoding at least a segment of the human immunoglobulin locus. The production and properties of animals having these properties are described in detail by e.g., Lonberg et al., WO93/12227; U.S. Pat. No. 5,545,806; and Kucherlapati, et al., WO91/10741; U.S. Pat. No. 6,150,584 (each of which is incorporated herein by reference in their entirety).

Various recombinant antibody library technologies may also be utilized to produce fully human antibodies. For example, one approach is to screen a library from human B cells according to the general protocol outlined by Huse et al., Science 246:1275-1281 (1989). Antibodies binding IP-10 or a fragment thereof are selected. Sequences encoding such antibodies (or binding fragments) are then cloned and amplified. The protocol described by Huse is rendered more efficient in combination with phage-display technology. See, e.g., Dower et al., WO 91/17271 and McCafferty et al., WO 92/01047; U.S. Pat. No. 5,969,108, (each of which is incorporated herein by reference in its entirety). In these methods, libraries of phage are produced in which members display different antibodies on their outer surfaces. Antibodies are usually displayed as Fv or Fab fragments. Phage displaying antibodies with a desired specificity are selected by affinity enrichment to IP-10 or fragment thereof.

Eukaryotic ribosome can also be used as a mean to display a library of antibodies and isolate the binding human antibodies by screening against the target antigen, such as IP-10, as described in Coia, G., et al., J. Immunol. Methods 1: 254 (1-2): 191-7 (2001); Hanes, J. et al., Nat. Biotechnol.: 18(12): 1287-92 (2000); Proc. Natl. Acad. Sci. U. S. A. 95(24): 14130-5 (1998); Proc. Natl. Acad. Sci. U. S. A. 94(10): 4937-42 (1997), each of which in incorporated by reference in its entirety.

The yeast system is also suitable for screening mammalian cell-surface or secreted proteins, such as antibodies. Antibody libraries may be displayed on the surface of yeast cells for the purpose of obtaining the human antibodies against a target antigen. This approach is described by Yeung, et al., Biotechnol. Prog. 18(2):212-20 (2002); Boeder, E. T., et al., Nat Biotechnol. 15(6):553-7 (1997), each of which is incorporated herein by reference in its entirety. Alternatively, human antibody libraries may be expressed intracellularly and screened via yeast two-hybrid system (WO 02/00729A2, which is incorporated herein by reference in its entirety).

Antigen-binding fragments of the anti-IP-10 antibodies, which retain the binding specificity to IP-10, are also included in the present invention. Examples include, but are not limited to, partial or full heavy chains or light chains, variable regions, or CDR regions of any anti-IP-10 antibodies described herein.

In a preferred embodiment of the invention, the antibody fragments are truncated chains (truncated at the carboxyl end). Preferably, these truncated chains possess one or more immunoglobulin activities (e.g., complement fixation activity). Examples of truncated chains include, but are not limited to, Fab fragments (consisting of the VL, VH, CL and CH1 domains); Fd fragments (consisting of the VH and CHI domains); Fv fragments (consisting of VL and VH domains of a single chain of an antibody); dab fragments (consisting of a VH domain); isolated CDR regions; (Fab')$_2$ fragments, bivalent fragments (comprising two Fab fragments linked by a disulphide bridge at the hinge region). The truncated chains can be produced by conventional biochemistry techniques, such as enzyme cleavage, or recombinant techniques, each of which is known in the art. These polypeptide fragments may be produced by proteolytic cleavage of intact antibodies by methods well known in the art, or by inserting stop codons at the desired locations in the vectors using site-directed mutagenesis, such as after CH1 to produce Fab fragments or after the hinge region to produce (Fab')$_2$ fragments. Single chain antibodies may be produced by joining $V_L$ and $V_H$-coding regions with a that encodes a peptide linker connecting the VL and VH protein fragments Since the immunoglobulin-related genes contain separate functional regions, each having one or more distinct biological activities, the genes of the antibody fragments may be fused to functional regions from other genes (e.g., enzymes, U.S. Pat. No. 5,004,692, which is incorporated herein by reference in its entirety) to produce fusion proteins (e.g., immunotoxins) or conjugates having novel properties.

The present invention comprises the use of anti-IP-10 antibodies in immunotoxins. Conjugates that are immunotoxins including antibodies have been widely described in the art. The toxins may be coupled to the antibodies by conventional coupling techniques or immunotoxins containing protein toxin portions can be produced as fusion proteins. The conjugates of the present invention can be used in a corresponding way to obtain such immunotoxins. Illustrative of such immunotoxins are those described by Byers, B. S. et al., Seminars Cell Biol. 2:59-70 (1991) and by Fanger, M. W. et al., Immunol Today 12:51-54 (1991).

Recombinant techniques can be used to produce the recombinant anti-IP-10 antibodies, as well as the chimeric or humanized anti-IP-10 antibodies or any other anti-IP-10 genetically-altered antibodies and the fragments or conjugate thereof in any expression systems including both prokaryotic and eukaryotic expression systems, such as bacteria, yeast, insect cells, plant cells, and mammalian cells (for example, NS0 cells).

Once produced, the whole antibodies, their dimers, individual light and heavy chains, or other immunoglobulin forms of the present invention can be isolated and purified according to standard procedures of the art, including ammonium sulfate precipitation, affinity columns, column chromatography, gel electrophoresis, and the like (see, generally, Scopes, R., Protein Purification (Springer-Verlag, N.Y., 1982)). Substantially pure immunoglobulins of at least about 90 to 95% homogeneity are preferred, and 98 to 99% or more homogeneity most preferred, for pharmaceutical uses. Once purified, partially or to homogeneity as desired, the polypeptides may then be used therapeutically (including extra corporeally) or in developing and performing assay procedures, immunofluorescent stainings, and the like. (See, generally, Immunological Methods, Vols. I and II, Lefkovits and Pernis, eds., Academic Press, NY, 1979 and 1981).

The antibodies of the present invention should typically be antagonistic. However, agonistic antibodies that trigger or enhance the IP-10 ligand or receptor functions are also included in the present invention. These antibodies will find use in the treatment of disorders caused by the hypo-activities of IP-10.

III. Therapeutic Uses

Antibodies of the present invention can be used to inhibit chemotaxis or migration of lymphocytes, such as T cells. The present invention includes a method of inhibiting chemotaxis of lymphocyte cells comprising contacting said lymphocyte cells with any of the antibodies or antibody fragments described herein. The antibodies can contact with the lymphocyte cells in vitro (such as in a cell culture environment) or iii vivo (such as in a subject). When the antibodies contact the lymphocytes in vitro, the antibodies can be added to the cell culture where the lymphocytes are cultivated. When the antibodies contact with the lymphocyte cells in vivo, the antibodies can be administered in a subject via the various routes described below.

Antibodies of the present invention are also useful for the prevention and/or treatment of autoimmune diseases, preferably IBD, including CD and UC. The present invention provides for a method of reducing the severity of at least one symptom of an inflammatory bowel disease comprising administering to a subject in need thereof an effective amount of an antagonist of IP-10, including all the antagonists described herein. Preferably, said antagonists are antibodies that bind to or neutralize human IP-10, and more preferably, the antibodies or antibody fragments or conjugates described herein.

The symptoms of IBD include, but are not limited to colon inflammatory lesions, body weight loss, diarrhea, and rectal prolapse. For measuring the severity of CD, subjects may be scored for Crohn's Disease Activity Index (hereinafter, "CDAI"). For measuring the severity of UC, subjects may be scored for Modified Truelove and Witts Severity Index (hereinafter, "MTWSI") and Mayo score. In addition, colon biopsy materials may be evaluated for inflammatory activities.

Therapeutic methods are usually applied to human patients but may be applied to other mammals.

There are various methods of administering the antagonists. The antagonists may be administered to a patient intravenously as a bolus or by continuous infusion over a period of time, by intramuscular, intraperitoneal, intra-cerebrospinal, subcutaneous, intra-articular, intrasynovial, intrathecal, oral, topical, inhalation routes, or other delivery means known to those skilled in the art.

The pharmaceutical compositions of the present invention commonly comprise a solution of antagonist, such as antibodies, or a cocktail thereof dissolved in an acceptable carrier, preferably an aqueous carrier. A variety of aqueous carriers can be used, e.g., water for injection (WFI), or water buffered with phosphate, citrate, acetate, etc. to a pH typically of 5.0 to 8.0, most often 6.0 to 7.0, and/or containing salts such as sodium chloride, potassium chloride, etc., to make isotonic. The carrier can also contain excipients such as human serum albumin, polysorbate 80, sugars or amino acids to protect the active protein. The concentration of an antibody in these formulations varies widely from about 0.1 to 100 mg/ml but is often in the range 1 to 10 mg/ml. The formulated antagonists such as monoclonal antibodies are particularly suitable for parenteral administration, and can be administered as an intravenous infusion or by subcutaneous, intramuscular or intravenous injection. Actual methods for preparing parentally administrable compositions are known or apparent to those skilled in the art and are described in more detail in, for example, Remington's Pharmaceutical Science (15th Ed., Mack Publishing Company, Easton, Pa., 1980), which is incorporated herein by reference. The present invention provides for a pharmaceutical composition comprising any one of the antibodies described herein.

The compositions can be administered for prophylactic and/or therapeutic treatments, comprising inhibiting the interactions between IP-10 and its receptors, inhibiting the IP-10 induced chemotaxis of lymphocytes, reducing the inflammatory responses, or reducing the clinical symptoms of IBD. An amount adequate to accomplish the desired effect is defined as an "effective amount". The antibodies can be delivered into a patient by single or multiple administrations.

For the purpose of treatment of disease, the appropriate dosage of the antibodies will depend on the severity and course of disease, the patient's clinical history and response, the toxicity of the antibodies, and the discretion of the attending physician. The antibodies are suitably administered to the patient at one time or over a series of treatments. The initial candidate dosage may be administered to a patient The proper dosage and treatment regimen can be established by monitoring the progress of therapy using conventional techniques known to the people skilled in the art.

Additionally, the antagonist (such as antibodies) can be utilized alone in substantially pure form, or together with therapeutic agents for autoimmune diseases known to those of skill in the art. Other therapies that may be used in conjunction with treatment with antibodies include administration of anti-sense nucleic acid molecules or biologicals, such as additional therapeutic antibodies. For the treatment of IBD, the antibody will often be administered after or in combination with one or more other immunosuppressive drugs or other therapies, for example, corticosteroids, cyclosporine, methotrexate, phototherapy. Thus, the treatment of the present invention is formulated in a manner allowing it to be administered serially or in combination with another agent for the treatment of inflammatory bowel diseases.

IV. Diagnostic Uses

Antibodies disclosed herein are useful in diagnostic and prognostic evaluation of diseases and disorders, particularly IBD (CD and/or UC) associated with IP-10 expression. At each stage of disease, monoclonal antibodies may be used to improve diagnostic accuracy and facilitate treatment decisions.

Methods of diagnosis can be performed in vitro using a cellular sample (e.g., blood sample, lymph node biopsy, or tissue) from a patient or can be performed by in vivo imaging.

In particular embodiments, the present invention provides an antibody conjugate wherein the antibodies of the present invention are conjugated to a diagnostic imaging agent Compositions comprising the antibodies of the present invention can be used to detect IP-10, for example, by radioimmunoassay, ELISA, FACS, etc. One or more labeling moieties can be attached to the antibodies. Exemplary labeling moieties include radiopaque dyes, radiocontrast agents, fluorescent molecules, spin-labeled molecules, enzymes, or other labeling moieties of diagnostic value, particularly in radiologic or magnetic resonance imaging techniques.

The present invention provides for a method of detecting IBD comprising detecting the differential expression of mRNA or protein of IP-10 in colon cells in a subject in need of such detection.

In one exemplary embodiment, the method of diagnosing CD or UC in a patient in need of such a diagnosis comprises: a) isolating a colon sample from said patient; b) contacting cells of said colon sample with the antibodies of the present invention; c) contacting normal colon cells with the antibodies of the present invention; and d) detecting and comparing the difference of the expression of IP-10 in said colon sample cells with the said normal colon cells. The normal cells can be the colon cells isolated from a healthy subject or a non-diseased portion of the colon of the same patient.

In another exemplary embodiment, the method of diagnosing CD or UC in a patient in need of such a diagnosis comprises detecting elevated serum level of IP-10 in the blood of the patient as compared with that of a healthy subject, for example, including the step of a) isolating a blood sample from a patient; b) contacting said blood sample with the antibodies of the present invention; c) contacting a blood sample from a healthy subject with the antibodies of the present invention; and d) detecting and comparing the serum IP-10 level of said patient with said healthy subject.

In addition to detecting IBD at pre- or early disease stage, the antibodies of the present invention can also be used to evaluate the treatment efficacy of a therapeutic approach, such as a method of treating IBD. Antibodies are utilized to detect the expression level of IP-10 before and after certain treatment. Reduction in IP-10 expression level may be an indicator of the effectiveness of the treatment.

The antibodies of the present invention can also be used as detecting agents in in vitro assays for research purposes. For example, the antibodies can be used to identify or isolate novel receptors or other binding proteins for IP-10 via the methods known in the art, such as by screening protein expression libraries.

The present invention also provides for a diagnostic kit comprising anti-IP-10 antibodies described herein. Such a diagnostic kit further comprises a packaged combination of reagents in predetermined amounts with instructions for performing the diagnostic assay. Where the antibody is labeled with an enzyme, the kit will include substrates and co-factors required by the enzyme. In addition, other additives may be included such as stabilizers, buffers and the like. The relative amounts of the various reagents may be varied widely to provide for concentrations in solution of the reagents that substantially optimize the sensitivity of the assay. Particularly, the reagents may be provided as dry powders, usually lyophilized, including excipients that, on dissolution, will provide a reagent solution having the appropriate concentration.

The following examples are offered by way of illustration and not by way of limitation. The disclosures of all citations in the specification are expressly incorporated herein by reference in their entirety.

EXAMPLES

Example 1

This example describes the over-expression of IP-10 mRNA in the IBD mouse model and patients.

RNA Isolation

Colon tissue samples from the diseased or control group mice were isolated, flushed with PBS, and snap-frozen in liquid nitrogen until use. To isolate RNA, the frozen tissues were ground into a fine powder using a mortar and pestle. Total RNA was extracted from the homogenized tissues using a standard Trizol method. All reagents and equipments used for isolation purposes were kept sterile. Total RNA was then treated -with DNase I enzyme from Ambion™ (Austin, Tex.) according to the manufacturer's protocol and stored at −80° C.

$1^{st}$ Strand cDNA Synthesis

The DNase treated RNA was then subjected to first strand cDNA synthesis using the SuperScript™ reverse transcriptase purchased from Invitrogen™ (Carlsbad, Calif.). The RNA was incubated with a random hexamer mix for 10 minutes at 70° C. and then cooled on ice for 5 minutes. The SuperScript™ reverse transcriptase, dNTP mix, DTT, RNasin, and the SuperScript™ buffer were then mixed together and allowed to be incubated at room temperature for 10 minutes. The reaction was carried out at 40° C. for 60 minutes. An equal volume of water was added to the reaction and allowed to be incubated at 95° C. for 10 minutes. The reaction was then cooled on ice for 5 min and stored at −20° C.

SYBR Green Real-Time PCR

All primers used for Real-Time PCR were designed using Primer Express Software™ and custom-ordered through QIAGEN OPERON™ (Alameda, Calif.). The reaction was set up in a 96-well Optical Reaction™ plate (ABI-Prism part #4306737) and sealed with Optical™ caps (8 caps/strip) (ABI-Prism™ part #4323032). The master mix used for the reaction was SYBR Green PCR Master Mix™ (Applied Biosystems™, Foster City, Calif., part #4309155), supplied at 2× concentration. The reaction was carried out in the GeneAmp 5700™ Sequence Detection System instrument. The first strand cDNA template described above was used at a $\frac{1}{250}$ dilution, in an amount of 2 µl per well in a 25 µl total reaction volume. A no-template control was set for each sample analyzed. β-Actin was used as an endogenous control for normalizing samples and sample variations. A standard curve was generated for each individual amplicon. Normalized expression values for a gene was calculated by the following equation: Mean Qty Sample A(Gene of Interest)/Mean Qty of Sample A (β-Actin). The fold change in expression of a gene of interest was obtained by using the equation: Normalized Expression Sample A/Normalized Expression Sample B.

cDNA Microarrays cDNA microarray technique was performed according to the manufacturer's instructions (Incyte Genomics™ and Agilent Technologies™, Palo Alto, Calif.).

To identify the differentially expressed genes in the inflammatory bowel diseases (IBD), we isolated colonic tissues from the mice afflicted with IBD. Total colon tissue was isolated, perfused in PBS, and snap-frozen in liquid nitrogen and stored until further use. RNA was isolated from the tissue and either total RNA or total mRNA was used for differential gene expression analysis. Using Agilent™ cDNA microarray analysis, we have determined that the mRNA for IP-10 elevated in colonic tissue isolated from the mice suffering from either of two distinct models of the inflammatory bowel disease, as compared to the levels of IP-10 mRNA present in colons from the nondiseased mice. RT-PCR analysis confirmed this difference. RT-PCR analysis of mRNA isolated from the diseased tissues obtained from both CD and UC patients revealed elevated levels of IP-10 mRNA, as compared to the level present in the nondiseased colonic tissues. Results indicated that murine models of IBD exhibited an overexpression of IP-10 as compared to control mice (see Example 7). Specifically, IP-10 mRNA exhibited a 5- to 16-fold increase in the diseased tissues of the CD patients, and a 7- to 11-fold increase in the diseased tissues of the UC patients, as compared to the mRNA isolated from the colonic tissues of the non-diseased individuals.

Example 2

This example describes the production of anti-IP-10 (AIP) monoclonal antibodies.

Immunogens for IP-10

Recombinant human IP-10 was purchased from R&D Systems™ (McKinley Place, N. Minneapolis, Minn.) and used to immunize Balb/c mice via either the intraperitoneal or footpad route. Briefly, mice were immunized intraperitoneally or in the hind footpads with 5-20 μg of protein with an equal volume of Ribi adjuvant in a total final volume of 20 μl. Footpad immunizations were performed 4 times at 4- or 5-day interval. Intraperitoneal immunization consisted of 4 immunizations at two-week intervals.

ELISA: Pre- and Post-immunization

Serum titers were determined by ELISA against human recombinant IP-10 with a standard antibody-capture ELISA assay and peroxidase-mediated detection. Serial dilutions of both pre-immune and post-immune serum were incubated with the capture protein and antigen-antibody complexes were detected with a horseradish peroxidase-conjugated anti-mouse-IgG secondary antibody and chromogenic reagent. Quantification of protein-specific serum titer was determined spectrophotometrically ($A_{415}$).

Fusion

The mice with highest sera-titers against the IP-10 protein were sacrificed. The popliteal, femoral, and sacral lymph nodes were removed from the foot-pad-immunized mice, whereas the spleens were removed from the intraperitoneally-immunized mice. Lymphocytes were isolated from the tissues and hybridomas were generated by standard procedures. Briefly, hybridomas were generated by polyethylene glycol (PEG) 1500 mediated fusion between lymphocytes and a murine myeloma cell line (NSO cells). Fused cells were plated into 96-well plates at a density of $10^5$ cells per plate. Selection of fused cells was accomplished with HAT (hypoxanthine, aminopterin, and thymidine) media.

Screening the Hybridomas

Reactivity of antibodies secreted by hybridomas was determined in an ELISA with human recombinant IP-10 as described above. Supernatants from the hybridoma wells were incubated in the wells coated with the recombinant human IP-10. Detection and quantitation of antigen-antibody interaction were achieved with the same methods as described above. Detection of positive wells was interpreted as hybridomas secreting a monoclonal antibody likely to have specificity for the human IP-10. Results indicated that a panel of antibodies designated as AIP 6, 8, 12, 13, 14, 18, 21, and 22 were reactive to the human IP-10.

Specificity of antibodies to the human IP-10 was confirmed by examining all the supernatants positive for binding to IP-10 for reactivity with the B lymphocyte chemokine (BLC), since IP-10 is a member of CXC chemokine family. However, the antibody designated as AIP18 displayed cross-reactivity to BLC. Reactivity of antibodies with the IP-10 proteins that are likely to be expressed in a native conformation was further determined by testing hybridoma supernatants on ELISA plates coated with the goat anti-human IP-10 antibody that had been incubated with the supernatants of the PHA-stimulated peripheral blood mononuclear cells (PBMC). Binding to the captured-PHA-blast-derived IP-10 established the reactivity with the native, mammalian cell-derived human IP-10.

Example 3

This example describes the blocking and neutralizing activities of the anti-IP-10 antibodies.

$1 \times 10^6$ CHO/CXCR3 transfectants (expressing high levels of CXCR3) were incubated for 60 minutes on ice with recombinant human IP-10 (2 ug/ml) and 50 ug/ml of purified anti-IP-10 monoclonal antibodies that have previously demonstrated binding to the human IP-10 by ELISA. The cells were then washed and incubated with biotin-labeled goat antibodies specific for the human IP-10 for 30 minutes on ice. Cells were washed, incubated with the phycoerythrin-conjugated streptaavidin, and incubated for 30 minutes on ice. Cells were washed again and the cell-surface-bound antibodies were detected by flow cytometry with Becton Dickinson FACScan™. Fluorescent profiles of cells incubated with the AIP antibodies against the human IP-10 mixtures were compared with the profiles of the cells incubated with both IP-10 and the control antibody. A decrease in the level of fluorescence between cells incubated with IP-10 and a control antibody as compared to IP-10 and AIP antibodies indicated inhibition of the interaction of IP-10 and the CXCR3 on the cell surface of CHO/CXCR3 cells. As shown in Table 1, more than 13 antibodies were tested, of which seven displayed a stronger inhibition of the interaction between IP-10 and CXCR3. In particular, the antibodies designated as AIP12, AIP13 and AIP10 were particularly effective in inhibiting IP-10 binding to CXCR3.

Example 4

This example describes a chemotaxis assay for identifying neutralizing anti-human IP-10 monoclonal antibodies.

Peripheral blood mononuclear cells were purified on Ficoll-Paque PLUS™ and washed thoroughly with RPMI+, which is RPMI-1640 medium plus 10% FBS plus L-Glutamine plus Antibiotic-Antimycotic. Cells were adjusted to 1 to $5 \times 10^6$/ml in RPMI+ and stimulated with PHA at 37° C./95% humidity/7.2% $CO^2$ for 3 days. Then the cells were split at 1:3 in RPMI+ and cultured in the presence of rIL-2 at 10 ng/ml for 3 more days. Alternatively, PHA blasts were used that were frozen but thawed and cultured overnight in RPMI+ with 10 ng/ml rIL-2. Cells were washed twice in a chemotaxis buffer, which is RPMI-1640+0.5% BSA+20 mM HEPES. Cells were adjusted to $1 \times 10^6$/ml in the chemotaxis buffer. rhIP-10 (R&D Systems™) at certain doses (500, 50 and 25 ng/ml) were mixed with the graded doses of AIP monoclonal antibodies for 30 to 60 minutes at room temperature. Control wells with rhIP-10 alone or without rhIP-10 were set up. 30 μl of the test reagent or control were added to the bottom chamber of the ChemoTx™ plate (Neuro Probe™, Gaithersburg, Md.) and then placed the filter frame on the plate so that the fluid made contact with the filter. The amount of 60 μl of cell suspension was placed on the filter top wells, covered, and incubated for 90 minutes at 37° C./95% humidity/7.2% $CO_2$. The non-migrating cells were removed by wiping the top of the filter with Kimwipes™. After centrifuge, cells were transferred from the microplates after assembly to an opaque-walled plate (Dynex™) and washed with 30 µl of buffer. 50 µl CellTiter-Glo™ (Promega™) were added and mixed for 2 minutes on a shaker. The plate was allowed to be incubated for another 10 minutes at room temperature. The luminescence on a Parkard LumiCount™ was read and recorded A panel of mouse anti-human-IP-10 monoclonal antibodies that bind to recombinant hIP-10 was generated. These antibodies also bind to supernatants from the PHA blasts. Several of the monoclonal antibodies against hIP-10 effectively neutralized the chemotaxis of PHA and LPS blasts in a dose-dependent manner. All of these monoclonal antibodies also bind to the mammalian-cell-expressed cynomolgus IP-10.

Exemplary neutralizing antibodies are the monoclonal antibodies: AIP13, AIP12, AIP8, AIP14, AIP6, AIP21, AIP5, AIP6, AIP17, and AIP18. All of these antibodies bind to IP-10 in ELISA and most of them block the binding of IP-10 to CXCR3 expressed on CHO/CXCR3 transfectants. All of these antibodies inhibit or completely block the IP-10-induced chemotaxis of PHA and LPS blasts. As shown in Table 1, as little as 80 ng/ml of AIP13, 100 ng/ml of AIP12, 127 ng/ml of AIP8, or 119 ng/ml of AIP14 inhibit the IP-10 (50 ng/ml)-induced chemotaxis of PHA blasts by 50%. AIP5, 6, 21, 32, and 36 are also potent neutralizing antibodies. The amino acid sequences of the mature heavy-chain and light-chain variable regions of AIP13 are presented here in SEQ ID NOs: 3 and 4, respectively. The amino acid sequences of the mature heavy-chain and light-chain variable regions of AIP12 are presented here in SEQ ID NOs: 41 and 42, respectively.

Example 5

This example describes the humanization of anti-IP-10 antibodies. Humanization of the murine monoclonal antibody AIP13 (MuAIP13) was carried out essentially according to the procedure of Queen, C., et al., Proc. Natl. Acad. Sci. USA 86: 10029-10033 (1989) and U.S. Pat. Nos. 5,585,089; 5,693,761; 5,693,762 and 6,180,370 (each of which is incorporated herein in its entirety). First, human V segments with high homology to the MuAIP13 VH or VL amino acid sequences were identified. Next, the CDR sequences together with framework amino acids important for maintaining the structures of the CDRs were grafted into the selected human framework sequences. In addition, human framework amino acids that were found to be rare in the corresponding V region subgroup were substituted with consensus amino acids to reduce potential immunogenicity. The resulting humanized monoclonal antibody, designated HuAIP13, was expressed in the mouse myeloma cell line NS0. Using a competitive binding assay with purified AIP 13 antibodies, the affinity of HuAIP13 to human IP-10 was shown to be approximately 2.8-fold lower than that of MuAIP13.

Materials and Methods

Cloning of Variable Region cDNAs

Total RNA was extracted from approximately $10^7$ hybridoma cells using TRIzol reagent (Life Technologies™, Inc., Rockville, Md.) and poly (A)+ RNA was isolated with the PolyATract mRNA Isolation System™ (Promega Corporation™, Madison, Wis.) according to the suppliers' protocols. Double-stranded cDNA was synthesized using the SMART RACE cDNA Amplification Kit™ (BD Biosciences Clontech™, Palo Alto, Calif.) following the supplier's protocol. The variable region cDNAs for the heavy and light chains were amplified by polymerase chain reaction (PCR) using 3' primers that anneal respectively to the mouse gamma and kappa chain C regions, and a 5' universal primer provided in the SMART RACE cDNA Amplification Kit™. For VH PCR, the 3' primer has the sequence 5'-GCCAGTGGATAGACT-GATGG-3' (SEQ ID NO: 71). For VL PCR, the 3' primer has the sequence 5'-GATGGATACAGTTGGTGCAGC-3' (SEQ ID NO: 72). The VH and VL cDNAs were subcloned into the pCR4Blunt-TOPO™ vector (Invitrogen Corporation™, Carlsbad, Calif.) for sequence determination. DNA sequencing was carried out by PCR cycle sequencing reactions with fluorescent dideoxy chain terminators (Applied Biosystems™, Foster City, Calif.) according to the manufacturer's instructions. The sequencing reactions were analyzed on a Model 377 DNA Sequencer™ (Applied Biosystems).

Humanization

Humanization of the antibody V regions was carried out as outlined by Queen, C., et al., Proc. Natl. Acad. Sci. USA 86: 10029-10033 (1989) and U.S. Pat. Nos. 5,585,089; 5,693,761; 5,693,762 and 6,180,370 (each of which is incorporated herein in its entirety). The human V region frameworks used as acceptors for the CDRs of MuAIP13 were chosen based on sequence homology. The computer programs ABMOD™ and ENCAD™ (Levitt, M., J. Mol. Biol. 168: 595-620 (1983)) were used to construct a molecular model of the variable regions. Amino acids in the humanized V regions predicted to have contact with the CDRs were substituted with the corresponding residues of MuAIP13. Amino acids in the humanized V region that were found to be rare in the same human V region subgroup were changed to human consensus amino acids to eliminate potential immunogenicity.

The heavy and light chain variable region genes were constructed and amplified using eight overlapping synthetic oligonucleotides ranging in length from approximately 65 to 80 bases (He, X.-Y., et al., J. Immunol. 160: 1029-1035 (1998)). The oligonucleotides were annealed pairwise and extended with the Klenow fragment of polymerase I, yielding four double-stranded segments. The resulting segments were denatured, annealed pairwise, and extended with Klenow fragment, yielding two segments. These segments were denatured, annealed pairwise, and extended once again, yielding a full-length gene. The resulting product was amplified by PCR using the Expand High Fidelity PCR System™ (Roche Diagnostics Corporation™, Indianapolis, Ind.). The PCR-amplified fragments were gel-purified, digested with MIUI and XbaI, gel-purified, and subcloned, respectively, into the pVg1.D.Tt vector as described in Cole, M. S., et al., J. Immunol. 159: 3613-3621 (1997) and the pHuCkappa.rgpt.dE vector as described in Kostelny, S. A., et al., Int. J. Cancer 93: 556-565 (2001). After sequence confirmation, the EcoRI fragment containing the entire heavy chain transcription unit was subcloned into the unique EcoRI site in the light chain expression vector, resulting in a single vector for expression of heavy and light chains.

Stable Transfection

Mouse myeloma cell line NS0 was obtained from the European Collection of Animal Cell Cultures (Salisbury, Wiltshire, UK), preadapted to Protein Free Basal Medium-1 (PFBM-1) (Protein Design Labs, Inc.™), and maintained in PFBM-1 at 37° C. in a 7.5% $CO_2$ incubator.

Stable transfection into NS0 was carried out by electroporation essentially as described in Bebbington, C. R., et al., Bio/Technology 10: 169-175 (1992). Before transfection, the expression vector was linearized using FspI. Approximately $10^7$ cells were transfected with 20 µg of linearized plasmid. The transfected cells were suspended in DME medium (BioWhittaker™, Inc., Walkersville, Md.) containing 10% FBS (HyClone™, Logan, Utah) and plated into several 96-well plates. After 48 hr, selection media (DME medium containing 10% FBS, HT media supplement, 0.5 mg/ml xanthine and 2.4 µg/ml mycophenolic acid) was applied. Approximately 10 days after the initiation of selection, culture supernatants were assayed for antibody production by ELISA. High-yielding NS0 transfectants were expanded in DME medium containing 10% FBS, then adapted to growth in serum-free medium using PFBM-1, expanded in PFBM-1 supplemented with Protein-Free Feed Medium-2 (PFFM-2) (Protein Design Labs, Inc.™), and grown to exhaustion.

Measurement of Antibody Expression by ELISA

Expression of HuAIP13 was measured by sandwich ELISA. MaxiSorp™ ELISA plates (Nunc Nalge International™, Rochester, N.Y.) were coated overnight at 4° C. with 100 µl/well of a 1:1000 dilution of AfffniPure™ goat anti-human IgG Foγ-chain specific polyclonal antibodies (Jackson ImmunoResearch Laboratories, Inc.™, West Grove, Pa.) in 0.2 M sodium carbonate-bicarbonate buffer, pH 9.4, washed with wash buffer (PBS containing 0.1% Tween 20), and blocked for 30 min at room temperature with 300 µl/well of SuperBlock Blocking Buffer™ in TBS (Pierce Chemical Company™, Rockford, Ill.). After washing with wash buffer, samples containing HuAIP13 were appropriately diluted in ELISA buffer (PBS containing 1% BSA and 0.1% Tween 20) and 100 µl/well was applied to the ELISA plates. As a standard, humanized IgG1/κ antibody HuM195, an anti-CD33 humanized monoclonal antibody developed at Protein Design Labs, Inc.™ and described in Co, M. S., et al., J. Immunol. 148: 1149-1154 (1992), was used. After incubating the plates for 1.5 hrs at room temperature, and washing with wash buffer, bound antibodies were detected using 100 µl/well of a 1:1000 dilution of HRP-conjugated AffiniPure™ goat anti-human IgG Fcγ-chain specific polyclonal antibodies (Jackson ImmunoResearch Laboratories, Inc.™). After incubating for 1 hr at room temperature, and washing with wash buffer, color development was performed by adding 100 µl/well of ABTS Peroxidase Substrate/Peroxidase Solution B™ (KPL, Inc.™, Gaithersburg, Md.). After incubating for 4 min at room temperature, color development was stopped by adding 100 µl/well of 2% oxalic acid. Absorbance was read at 415 mn using a VersaMax™ microplate reader (Molecular Devices Corporation™, Sunnyvale, Calif.).

Purification of Anti-IP-10 Antibodies

NS0 stable transfectants were grown to exhaustion in PFBM-1 supplemented with PFFM-2. After centrifugation and filtration, culture supernatant was loaded onto a protein-A Sepharose column. The column was washed with PBS before the antibody was eluted with 0.1 M glycine-HCl (pH 2.8), 0.1 M NaCl. After neutralization with 1 M Tris-HCl (pH 8), the eluted protein was dialyzed against PBS and stored at 4° C. Antibody concentration was determined by measuring absorbance at 280 nm (1 mg/ml=1.4 $A_{280}$). SDS-PAGE in Tris-glycine buffer was performed according to standard procedures.

Competition ELISA

MaxiSorp™ ELISA plates (Nalge Nunc International™) were coated overnight at 4° C. with 100 µl/well of 0.25 µg/ml human IP-10 (R&D Systems, Inc.™, Minneapolis, Minn.) in 0.2 M sodium carbonate-bicarbonate buffer, pH 9.4, washed with wash buffer (PBS containing 0.1% Tween 20), and blocked for 30 min at room temperature with 300 µl/well of SuperBlock Blocking Buffer™ in TBS (Pierce Chemical Company™). After washing with wash buffer, a mixture of biotinylated MuAIP13 (0.5 µg/ml final concentration) and competitor antibody (MuAIP13 or HuAIP13 starting at 250 µg/ml final concentration and serially diluted 3-fold) in 100 µl/well of ELISA buffer was added in triplicate. As isotype controls, 100 µl/well of 250 µg/ml mouse IgG1/κ (MuFd79) or humanized IgG1/κ (HuM291) monoclonal antibodies in ELISA buffer was used. As a no-competitor control, 100 µl/well of ELISA Buffer was used. After incubating the plates for 1.5 hrs at room temperature, and washing with wash buffer, bound antibodies were detected using 100 µl/well of 1 µg/ml HRP-conjugated streptavidin (Pierce Chemical Company™) in ELISA buffer. After incubating for 1 hr at room temperature, and washing with wash buffer, color development was performed by adding 100 µl/well of ABTS Peroxidase Substrate/Peroxidase Solution B™ (KPL, Inc.™). After incubating for 4 min at room temperature, color development was stopped by adding 100 µl/well of 2% oxalic acid. Absorbance was read at 415 nm.

Results

Cloning and Sequencing of MuAIP13 V-region cDNAs

The MuAIP13 heavy and light chain V-region cDNAs were cloned from the hybridoma cells as described in Materials and Methods. Several heavy and light chain clones were sequenced from two independent PCR reactions. Unique sequences homologous to typical mouse heavy and light chain variable regions were identified. The predicted amino acid sequences of the mature heavy and light chain variable regions are depicted in SEQ ID NO. 3 and SEQ ID NO. 4, respectively. The cDNA sequences encoding the heavy and light chain V-regions are depicted in SEQ ID NO. 11 and SEQ ID NO. 12, respectively.

Humanization of Antibodies

For humanization of the MuAIP13 variable regions, the general approach provided in the present invention was followed. First, a molecular model of the MuAIP13 variable regions was constructed with the aid of the computer programs ABMOD™ and ENCAD™ (Levitt, M., J. Mol. Biol. 168: 595-620 (1983)). Next, based on a homology search against human V and J segment sequences, the VH segment DP-3 (Tomlinson, I. M., et al., J. Mol. Biol. 227: 776-789 (1992)) and the J segment JH6 (Ravetch, J. V., et al., Cell 27: 583-591 (1981)) were selected to provide the frameworks for the HuAIP13 heavy chain variable region. For the HuAIP13 light chain variable region, the VL segment DPK1 (Cox, J. P. L., et al., Eur. J. Immunol. 24: 827-836 (1994)) and the J segment JK2 (Hieter, P. A., et al., J. Biol. Chem. 257: 1516-1522 (1982)) were used. The identity of the framework amino acids between MuAIP13 VH and the acceptor human DP-3 and JH6 segments was 69%, while the identity between MuAIP13 VL and the acceptor human DPK1 and JK2 segments was 78%.

At framework positions in which the computer model suggested significant contact with the CDRs, the amino acids from the V regions were substituted for the original human framework amino acids. This was done at residues 46, 68, 70, 72, and 98 of the heavy chain. For the light chain, replacements were made at residues 48, 49, 58, 69, and 71. Framework residues that occurred only rarely at their respective positions in the corresponding human V region subgroups were replaced with human consensus amino acids at those positions. This was done at residues 38 and 77 of the heavy chain.

Expressions of the HuAIP13 IgG1/κ Antibody

Genes encoding humanized VH or VL were designed as mini-exons including signal peptides, splice donor signals, and appropriate restriction enzyme sites for subsequent cloning into a mammalian expression vector. The splice donor signals in the VH and VL mini-exons were derived from the corresponding human germline JH and JK sequences, respectively. The signal peptide sequence in the humanized VH mini-exon was derived from the MuEP5C7 VH (He, X.-Y., et al., supra); the signal peptide sequence in the humanized VL mini-exon was derived from the corresponding MuAIP13 VL. The HuAIP13 VH and VL genes were constructed by extension of eight overlapping synthetic oligonucleotides and PCR amplification. A series of 8 overlapping oligonucleotides (1-8) was used. Oligonucleotides 1 and 2, 3 and 4, 5 and 6, and 7 and 8 were separately annealed and extended with the Klenow fragment of polymerase I. The resulting double-stranded DNA segments, A and B, and C and D, were separately mixed, denatured, annealed and extended to yield the DNA segments E and F, respectively, which were then mixed to generate the entire mini-exon (G) in the third annealing-and-extension step. The mini-exon was amplified by PCR with primers 9 and 10 to incorporate the flanking MiuI and XbaI sites. Primers H1-10 for the synthesis of the humanized heavy chain variable region are presented in SEQ ID NOs: 21-30, respectively. Primers L1-10 for the synthesis of the humanized light chain variable region are presented in SEQ ID NOs: 31-40, respectively.

The resulting V gene fragments were cloned into the mammalian expression vectors pHuCkappa.rgpt.dE and pVg1.D.Tt (described, supra), and then combined to generate a single expression vector for co-expression of the light and heavy chains. The DNA sequences of the humanized VL and VH mini-exons are depicted in SEQ ID Nos: 17 and 19, respectively, and deduced amino acid sequences of the humanized VL and VH mini-exons are depicted in SEQ ID Nos: 18 and 20, respectively.

To obtain cell lines stably producing HuAIP13, the single expression vector was introduced into the chromosome of mouse myeloma cell line NS0 by electroporation. Stable transfectants were selected for gpt expression as described in Materials and Methods. Culture supernatants of NS0 stable transfectants were analyzed by ELISA for production of HuAIP13. One of the high producing cell lines, clone DB2, was adapted to and expanded in PFBM-1 supplemented with PFFM-2. HuAIP13 IgG1/κ monoclonal antibody was purified from spent culture supernatant with a protein-A Sepharose column as described in Materials and Methods, supra. SDS-PAGE analysis under non-reducing conditions indicated that HuAIP13 has a molecular weight of about 150-160 kD. Analysis under reducing conditions indicated that HuAIP13 is comprised of a heavy chain with a molecular weight of about 50 kD and a light chain with a molecular weight of about 25 kD). The purity of the antibody appeared to be more than 95%.

Binding Properties of HuAIP13

The affinity of HuAIP13 to human IP-10 was analyzed by competition ELISA as described in Materials and Methods, supra. results indicated that both MuAIP13 and HuAIP13 bind to human recombinant IP-10; mediated inhibition of IP-10 binding to CXCR3; and inhibited IP-10 mediated chemotaxis of recombinant human IP-10, native human IP-10 and cynomolgous IP-10. furthermore, results indicated that both MuAIP13 and HuAIP13 competed with biotinylated MuAIP13 and MuAIP13 in a concentration-dependent manner. As shown in Table 1, the mean $IC_{50}$ values of MuAIP13 and HuAIP13, obtained using the computer software Graph-Pad Prism™ (GraphPad Software Inc.™, San Diego, Calif.), were 2.1 µg/ml and 5.8 µg/ml, respectively. The binding of HuAIP13 to human IP-10 was approximately 2.8-fold less than that of MuAIP13. These results clearly indicate that humanization of mouse anti-IP-10 monoclonal antibody AIP13 was successful: HUAIP13 retained binding affinity to human IP-10.

HUAIP13 also blocks the binding of IP-10 to CXCR3 and exhibits nanomolar affinity for IP-10 (Table 4). HuAIP13 also inhibits IP-10 mediated chemotaxis with a comparable $IC_{50}$ (~100 ng/ml) and inhibits 100% of IP-10 mediated chemotaxis at <1 µg/ml.

TABLE 1

AFFINITY OF HuAIP13 TO HUMAN IP-10

| Competitor | Exp. A | Exp. B | Exp. C | Average | Std. Dev. |
|---|---|---|---|---|---|
| MuAIP13 | 2.1 | 2.4 | 1.8 | 2.1 | 0.3 |
| HuAIP13 | 6.1 | 6.5 | 4.8 | 5.8 | 0.8 |
| Difference | 2.9 fold | 2.7 fold | 2.7 fold | 2.8 fold | |

Example 6

This example describes the humanization of anti-IP-10 antibodies. Humanization of the murine monoclonal antibody AIP12 (MUAIP12) was carried out essentially according to the procedure of Queen, C., et al., Proc. Natl. Acad. Sci. USA 86: 10029-10033 (1989) and U.S. Pat. Nos. 5,585,089; 5,693,761; 5,693,762 and 6,180,370 (each of which is incorporated herein in its entirety). First, human V segments with high homology to the MuAIP12 VH or VL amino acid sequences were identified. Next, the CDR sequences together with framework amino acids important for maintaining the structures of the CDRs were grafted into the selected human framework sequences. In addition, human framework amino acids that were found to be rare in the corresponding V region subgroup were substituted with consensus amino acids to reduce potential immunogenicity. The resulting humanized monoclonal antibody, designated HUAIP12, was expressed in the mouse myeloma cell line NS0. Using a competitive binding assay with purified AIP12 antibodies, the affinity of HuAIP12 to human IP-10 was shown to be approximately 2.5-fold lower than that of MuAIP12.

Materials and Methods

Cloning of Variable Region cDNAs

Total RNA was extracted from approximately $10^7$ hybridoma cells using TRIzol™ reagent (Life Technologies, Inc.™, Rockville, Md.) and poly (A)+ RNA was isolated with the FastTrack 2.0 mRNA Isolation Kit™ (Invitrogen Corporation™, Carlsbad, Calif.) according to the suppliers' protocols. Double-stranded cDNA was synthesized using the SMART RACE cDNA Amplification Kit™ (BD Biosciences Clontech™, Palo Alto, Calif.) following the supplier's protocol. The variable region cDNAs for the heavy and light chains were amplified by polymerase chain reaction (PCR) using 3' primers that anneal respectively to the mouse gamma and kappa chain C regions, and a 5' universal primer provided in the SMART RACE cDNA Amplification Kit™. For VH PCR, the 3' primer has the sequence 5'-GCCAGTGGATA-GACTGATGG-3' (SEQ ID NO: 71). For VL PCR, the 3' primer has the sequence 5'-GATGGATACAGTTGGTG-CAGC-3' (SEQ ID NO: 72). The VH and VL cDNAs were subcloned into the pCR4Blunt-TOPO™ vector (Invitrogen Corporation™, Carlsbad, Calif.) for sequence determination. DNA sequencing was carried out by PCR cycle sequencing reactions with fluorescent dideoxy chain terminators (Applied Biosystem™, Foster City, Calif.) according to the manufacturer's instructions. The sequencing reactions were analyzed on a Model 377 DNA Sequencer™ (Applied Biosystems™).

Humanization

Humanization of the antibody V regions was carried out as outlined by Queen, C., et al., Proc. Natl. Acad. Sci. USA 86: 10029-10033 (1989) and U.S. Pat. Nos. 5,585,089; 5,693,761; 5,693,762 and 6,180,370 (each of which is incorporated herein in its entirety). The human V region frameworks used as acceptors for the CDRs of MuAIP12 were chosen based on sequence homology. The computer programs ABMOD™ and ENCAD™ (Levitt, M., J. Mol. Biol. 168: 595-620 (1983)) were used to construct a molecular model of the variable regions. Amino acids in the humanized V regions predicted to have contact with the CDRs were substituted with the corresponding residues of MuAIP12. Amino acids in the humanized V region that were found to be rare in the same V region subgroup were changed to consensus amino acids to eliminate potential immunogenicity.

The heavy and light chain variable region genes were constructed and amplified using eight overlapping synthetic oligonucleotides ranging in length from approximately 65 to 80 bases according to the method described in He, X.-Y., et al., J. Immunol. 160: 1029-1035 (1998). The oligonucleotides were annealed pairwise and extended with the Klenow fragment of DNA polymerase I, yielding four double-stranded segments. The resulting segments were denatured, annealed pairwise, and extended with Klenow fragment, yielding two segments. These segments were denatured, annealed pairwise, and extended once again, yielding a full-length gene. The resulting product was amplified by PCR using the Expand High Fidelity PCR System™ (Roche Diagnostics Corporation™, Indianapolis, Ind.). The PCR-amplified fragments were gel-purified, digested with MluI and XbaI, gel-purified, and sub-cloned respectively into the pVg1.D.Tt vector (Cole, M. S., et al., J. Immunol. 159: 3613-3621 (1997)) and the pHuCkappa.rgpt.dE vector (Kostelny, S. A., et al., Int J. Cancer 93: 556-565 (2001)). After sequence confirmation, the EcoRI fragment containing the entire heavy chain transcription unit was subcloned into the unique EcoRI site in the light chain expression vector, resulting in a single vector for expression of heavy and light chains.

Stable Transfection

Mouse myeloma cell line NS0 was obtained from the European Collection of Animal Cell Cultures (Salisbury, Wiltshire, UK), preadapted to Protein Free Basal Medium-1 (PFBM-1) (Protein Design Labs, Inc.™), and maintained in PFBM-1 at 37° C. in a 7.5% $CO_2$ incubator.

Stable transfection into NS0 was carried out by electroporation essentially as described in Bebbington, C. R., et al., Bio/Technology 10: 169-175 (1992). Before transfection, the expression vector was linearized using FspI. Approximately $10^7$ cells were transfected with 20 µg of linearized plasmid. The transfected cells were suspended in DME medium (Bio-Whittaker, Inc.™, Walkersville, Md.) containing 10% FBS (HyClone™, Logan, Utah) and plated into several 96-well plates. After 48 hr, selection media (DME medium containing 10% FBS, HT media supplement, 0.5 mg/ml xanthine and 2.4 µg/ml mycophenolic acid) was applied. Approximately 10 days after the initiation of selection, culture supernatants were assayed for antibody production by ELISA. High-yielding NSO transfectants were maintained in PFBM-1, expanded in PFBM-1 supplemented with Protein-Free Feed Medium-2 (PFFM-2) (Protein Design Labs, Inc.™), and grown to exhaustion.

Measurement of Antibody Expression by ELISA

Expression of HuAIP12 was measured by sandwich ELISA. MaxiSorp™ ELISA plates (Nunc Nalge International™, Rochester, N.Y.) were coated overnight at 4° C. with 100 µl/well of a 1:1000 dilution of AffiniPure™ goat anti-human IgG Fcγ-chain specific polyclonal antibodies (Jackson ImmunoResearch Laboratories, Inc.™, West Grove, Pa.) in 0.2 M sodium carbonate-bicarbonate buffer, pH 9.4, washed with Wash Buffer (PBS containing 0.1% Tween 20), and blocked for 30 min at room temperature with 300 µl/well of SuperBlock Blocking Buffer™ in TBS (Pierce Chemical Company™, Rockford, Ill.). After washing with Wash Buffer, samples containing HuAIP12 were appropriately diluted in ELISA Buffer (PBS containing 1% BSA and 0.1% Tween 20) and 100 µl/well was applied to the ELISA plates. As a standard, humanized IgG1/κ antibody HuAIP13, described, supra, was used. After incubating the plates for 1.5 hrs at room temperature, and washing with wash buffer, bound antibodies were detected using 100 µl/well of a 1:1000 dilution of HRP-conjugated AffiniPure™ goat anti-human IgG Fcγ-chain specific polyclonal antibodies (Jackson ImmunoResearch Laboratories™, Inc.). After incubating for 1 hr at room temperature, and washing with wash buffer, color development was performed by adding 100 µl/well of ABTS Peroxidase Substrate/Peroxidase Solution B™ (KPL, Inc.™, Gaithersburg, Md.). After incubating for 4 min at room temperature, color development was stopped by adding 100 µL/well of 2% oxalic acid. Absorbance was read at 415 nm using a VersaMax™ microplate reader (Molecular Devices Corporation™, Sunnyvale, Calif.).

Purification of Anti-IP-10 Antibodies

NS0 stable transfectants were grown to exhaustion in PFBM-1 supplemented with PFFM-2. After centrifugation and filtration, culture supernatant was loaded onto a protein-A Sepharose column. The column was washed with ImmunoPure (A)™ IgG binding buffer (Pierce Chemical Company™) before the antibody was eluted with 0.1 M glycine-HCl (pH 2.7), 0.1 M NaCl. After neutralization with 1 M Tris-HCl (pH 8), the eluted protein was dialyzed against PBS, further fractionated by size exclusion chromatography to achieve monomer, 0.2 µm filtered and stored at 4° C. Antibody concentration was determined by measuring absorbance at 280 nm (1 mg/ml=1.4 $A_{280}$). SDS-PAGE in Tris-glycine buffer was performed according to standard procedures.

Competition ELISA

MaxiSorp™ ELISA plates (Nalge Nunc International™) were coated overnight at 4° C. with 100 µl/well of 0.25 µg/ml human IP-10 (R&D Systems, Inc.™, Minneapolis, Minn.) in 0.2 M sodium carbonate-bicarbonate buffer, pH 9.4, washed with wash buffer (PBS containing 0.1% Tween 20), and blocked for 30 min at room temperature with 300 µl/well of SuperBlock Blocking Buffer™ in TBS (Pierce Chemical Company™). After washing with wash buffer, a mixture of biotinylated MUAIP12 (0.7 µg/ml final concentration) and competitor antibody (MuAIP12 or HuAIP12 starting at 400 µg/ml final concentration and serially diluted 3-fold) in 100 µl/well of ELISA buffer was added in triplicate. As isotype controls, 100 µl/well of 250 µg/ml mouse IgG1/κ (MuFd79) or humanized IgG1/κ (HuFd79) monoclonal antibodies in ELISA buffer was used. As a no-competitor control, 100 µl/well of ELISA Buffer was used. After incubating the plates for 1.5-2 hrs at room temperature, and washing with wash buffer, bound antibodies were detected using 100 µl/well of 1 µg/ml HRP-conjugated streptavidin (Pierce Chemical Company™) in ELISA buffer. After incubating for 1 hr at room temperature, and washing with Wash Buffer, color development was performed by adding 100 µl/well of ABTS Peroxidase Substrate/Peroxidase Solution B™ (KPL, Inc.). After incubating for 4 min at room temperature, color development was stopped by adding 100 µl/well of 2% oxalic acid. Absorbance was read at 415 nm.

Results

Cloning and Sequencing of MuAIP12 V-region cDNAs

The MuAIP12 heavy and light chain V-region cDNAs were cloned from the hybridoma cells as described in Materials and Methods. Several heavy and light chain clones were sequenced from two independent PCR reactions. Unique sequences homologous to typical mouse heavy and light chain variable regions were identified. The predicted amino acid sequences of the mature heavy and light chain variable regions are depicted in SEQ ID NO. 41 and SEQ ID NO. 42, respectively. The cDNA sequences encoding the heavy and light chain variable regions are depicted in SEQ ID NO. 43 and SEQ ID NO. 44, respectively.

Humanization of Antibodies

For humanization of the MuAIP12 variable regions, the general approach provided in the present invention was followed. First, a molecular model of the MuAIP12 variable regions was constructed with the aid of the computer programs ABMOD™ and ENCAD™ (Levitt, M., J. Mol. Biol. 168: 595-620 (1983)). Next, based on a homology search against human V and J segment sequences, the VH segment DP-3 (Tomlinson, I. M., et al., J. Mol. Biol 227: 776-789 (1992)) and the J segment JH6 (Ravetch, J. V., et al., Cell 27: 583-591 (1981)) were selected to provide the frameworks for the HuAIP12 heavy chain variable region. For the HuAIP12 light chain variable region, the VL segment DPK1 (Cox, J. P. L., et al., Eur. J. Immunol. 24: 827-836 (1994)) and the J segment JK2 (Hieter, P. A., et al., J. Biol. Chem. 257: 1516-1522 (1982)) were used. The identity of the framework amino acids between MuAIP12 VH and the acceptor human DP-3 and JH6 segments was 69%, while the identity between MuAIP12 VL and the acceptor human DPK1 and JK2 segments was 80%.

At framework positions in which the computer model suggested significant contact with the CDRs, the amino acids from the V regions were substituted for the original human framework amino acids. This was done at residues 46, 68, 70, 72, and 98 of the heavy chain. For the light chain, replacements were made at residues 49, 58, 69, and 71. Framework residues that occurred only rarely at their respective positions in the corresponding human V region subgroups were replaced with human consensus amino acids at those positions. This was done at residues 38 and 77 of the heavy chain.

Expression of the HuAIP12 IgG1/κ Antibody

Genes encoding humanized VH or VL were designed as mini-exons including signal peptides, splice donor signals, and appropriate restriction enzyme sites for subsequent cloning into a mammalian expression vector. The splice donor signals in the VH and VL mini-exons were derived from the corresponding human germline JH and JK sequences, respectively. The signal peptide sequence in the humanized VH mini-exon was derived from the MuEP5C7 VH (He, X.-Y., et al., supra); the signal peptide sequence in the humanized VL mini-exon was derived from the corresponding MuAIP12 VL. The HuAIP12 VH and VL genes were constructed by extension of eight overlapping synthetic oligonucleotides and PCR amplification. A series of 8 overlapping oligonucleotides (1-8) was used. Oligonucleotides 1 and 2, 3 and 4, 5 and 6, and 7 and 8 were separately annealed and extended with the Klenow fragment of DNA polymerase I. The resulting double-stranded DNA segments, A and B, and C and D, were separately mixed, denatured, annealed and extended to yield the DNA segments E and F, respectively, which were then mixed to generate the entire mini-exon (G) in the third annealing-and-extension step. The mini-exon was amplified by PCR with primers 9 and 10 to incorporate the flanking MluI and XbaI sites. Primers 12H1-10 for the synthesis of the humanized heavy chain variable region are presented in SEQ ID NOs: 51-60, respectively. Primers 12L1-10 for the synthesis of the humanized light chain variable region are presented in SEQ ID NOs: 61-70, respectively.

The resulting V gene fragments were cloned into the mammalian expression vectors pHuCkappa.rgpt.dE and pVg1.D.Tt, described, supra, and then combined to generate a single expression vector for co-expression of the light and heavy chains. The sequences of the humanized VL and VH mini-exons are depicted in SEQ ID Nos: 47 and 49, respectively, and the deduced amino acid sequences of the humanized VL and VH mini-exons are depicted in SEQ ID Nos: 48 and 50, respectively.

To obtain cell lines stably producing HuAIP12, the single expression vector was introduced into the chromosome of mouse myeloma cell line NS0 by electroporation. Stable transfectants were selected for gpt expression as described in Materials and Methods, supra. Culture supernatants of NS0 stable transfectants were analyzed by ELISA for production of HuAIP12. One of the high producing cell lines, clone #4, was adapted to and expanded in PFBM-1 supplemented with PFFM-2. HuAIP12 IgG1/κ monoclonal antibody was purified from spent culture supernatant with a protein-A Sepharose column as described in Materials and Methods, supra. SDS-PAGE analysis under non-reducing conditions indicated that HuAIP12 has a molecular weight of about 150-160 kD. Analysis under reducing conditions indicated that HuAIP12 is comprised of a heavy chain with a molecular weight of about 50 kD and a light chain with a molecular weight of about 25 kD. The purity of the antibody appeared to be more than 95%.

Binding Properties of HuAIP12

The affinity of HuAIP12 to human IP-10 was analyzed by competition ELISA as described in Materials and Methods, supra. Results indicated that both MuAIP13 and HuAIP13 bind to human recombinant IP-10; mediated inhibition of IP-10 binding to CXCR3; and inhibited IP-10 mediated chemotaxis of recombinant human IP-10, native human IP-10, and cynomolgous IP-10. Furthermore, results indicated that MuAIP12 and HuAIP12 competed with biotinylated MuAIP13 and MuAIP12 in a concentration-dependent manner. As shown in Table 2, the average $IC_{50}$ values of MuAIP12 and HuAIP12, obtained using the computer software GraphPad Prism™ (GraphPad Software Inc.™, San Diego, Calif.), were 5.4 µg/ml and 13.5 µg/ml, respectively. The binding of HuAIP12 to human IP-10 was approximately 2.5-fold less than that of MuAIP12. These results clearly indicate that humanization of mouse anti-IP-10 monoclonal antibody AIP12 was successful: HuAIP12 retained binding affinity to human IP-10. Further, these results indicate that HuAIP12 has a 2-3 fold higher affinity than HuAIP13 for IP-10 (Table 3).

HuAIP12 also blocks the binding of IP-10 to CXCR3 and exhibits nanomolar affinity for IP-10. HuAIP12 also inhibits IP-10 mediated chemotaxis with a comparable $IC_{50}$ (~100 ng/ml) and inhibits 100% of IP-10 mediated chemotaxis at <1 µg/ml (Table 4).

TABLE 2

AFFINITY OF HuAIP12 TO HUMAN IP-10

| Competitor | Exp. A | Exp. B | Exp. C | Exp. D | Average | Std. Dev. |
|---|---|---|---|---|---|---|
| MuAIP12 | 6.5 | 4.4 | 6.6 | 4.2 | 5.4 | 0.3 |
| HuAIP12 | 18.6 | 10.7 | 14.5 | 10.3 | 13.5 | 3.9 |
| Difference | 2.9 fold | 2.4 fold | 2.2 fold | 2.4 fold | 2.5 fold | |

TABLE 3

AFFINITY OF HUMANIZED AIP TO HUMAN IP-10

| ANTIBODY | $k_a$ (1/MS) | $k_d$ (1/s) | $K_D$ (nM) |
|---|---|---|---|
| AIP12 | $1.05 \times 10^6$ | $2.82 \times 10^{-4}$ | 0.275 |
| HuAIP12 | $7.55 \times 10^5$ | $3.57 \times 10^{-4}$ | 0.472 |
| AIP13 | $1.58 \times 10^5$ | $1.96 \times 10^{-4}$ | 1.24 |
| HuAIP13 | $1.56 \times 10^5$ | $1.94 \times 10^{-4}$ | 1.24 |

TABLE 4

MINIMAL DONOR TO DONOR VARIATION INHIBITION OF CHEMOTAXIS ($IC_{50\%}$) VALUES FOR MULTIPLE DONORS ON RECOMBINANT IP-10)

| Donor # | AIP12 | HuAIP12 | AIP13 | HuAIP13 |
|---|---|---|---|---|
| 215 | 130 | 142 | 260 | 139 |
| 1022 | 135 | 145 | 229 | 130 |
| 1022 | 51 | 43 | 154 | 29 |
| 318 | 41 | 38 | 139 | 45 |
| 1022 | 86 | 74 | 78 | 75 |
| 1012 | 91 | 73 | 84 | 77 |
| Mean ± SD | 89 ± 39 | 86 ± 47 | 157 ± 74 | 86 ± 44 |

All values in ng/ml.

Example 7

This example describes the treatment of IBD with humanized anti-IP-10 antibodies in one or two different IBD mouse models. Two mouse models of IBD used herein are the spontaneous colitis model and the adoptive transfer model.
Spontaneous colitis model IL-10 knockout model For the spontaneous model, IL-10-deficient NOD mice (Jackson Laboratories™, Bar Harbor, Me.) are used. The age-matched NOD mice are used as the control group mice. The IL-10-deficient NOD mice develop IBD between 8-12 weeks. This IBD has been characterized as Th1 mediated and it resembles CD in humans. IL-10-KO (knockout) mice exhibit an increased expression of IP-10 as compared to the control mice.
CD4/CD45RB$^{hi}$ Adoptive Transfer Model For the transfer model, CD4/CD45RB$^{hi}$ T cells from naive syngeneic BALB/c mice are isolated and injected at 3 to $4 \times 10^5$/mouse intravenously into CB17.SCID mice. Following the transfer, the recipient mice develop IBD. This IBD has been characterized as Th1 mediated and it resembles CD in humans. Age-matched, non-diseased CB17.SCID mice are used as the control group mice. Mice are considered positive for the disease based on the development of one or more of the following clinical symptoms such as body weight loss, diarrhea, and rectal prolapse. The CD4/CD45RB$^{hi}$ mice exhibit an increased expression of IP-10 as compared to the control mice. Further, the CD4/CD45RB$^{hi}$ mice experience weight loss (between 10-20%) at least 2 weeks post transfer as compared to control mice.

Following the transfer of CD4 T cells from the diseased IL-10-KO-NOD mice into NOD.SCID mice and/or CD4/CD45RB$^{hi}$ BALB/c T cells into CB17.SCID mice, the recipient mice are treated at weekly intervals with humanized anti-mouse-IP-10 polyclonal antibodies or monoclonal antibodies (0.5 to 1 mg mg/dose in PBS, intraperitoneal route). The control group mice receive isotype-matched IgG or pre-immune polyclonal IgG. In a separate set of experiments, the therapeutic efficacy of the neutralizing anti-IP-10 antibody is tested once the recipient mice develop the disease (based on their body weight loss with respect to the initial body weight).

The mice are monitored for clinical signs of disease such as loss of body weight, diarrhea, and rectal prolapse. Colon samples are harvested from the mice for histological examination by H&E staining.

Example 8

This example describes the generation of a high affinity anti-human IP-10 monoclonal antibody.
Characterization of Humanized Anti-IP-10 Monoclonal Antibodies HuAIP12 and HuAIP13

HuAIP12 and HUAIP13 are humanized IgG1/κ forms of the murine monoclonal antibodies AIP12 and AIP13, respectively, which bind to and neutralize human IP-10 (Examples 5 and 6). The VL and VH amino acid sequences of HuAIP12 are shown in SEQ ID NOS. 46 and 45, respectively. The VL and VH amino acid sequences of HuAIP13 are shown in SEQ ID NOS. 15 and 13, respectively. Biacore™ analysis indicated that the binding affinity of HuAIP12 to human IP-10 is approximately 2.6 fold higher than that of HuAIP13 (Table 3).

The epitopes recognized by HuAIP12 and HuAIP13 on human IP-10 were found to overlap with each other. In competition ELISA experiments, binding of AIP13 to human IP-10 was blocked by both HuAIP12 and HuAIP13 in a concentration-dependent manner. The $IC_{50}$ value for HuAIP12 was 3.1 µg/ml and the $IC_{50}$ value for HuAIP13 was 9.2 µg/ml.

Alignment of the V region sequences revealed that there were only two amino acid differences between the mature HuAIP12 and HuAIP13 VH regions: one in CDR2 and one in CDR3 (FIG. 1A). In addition, it was found that there were only four amino acid differences between the mature HuAIP12 and HuAIP13 VL regions: one in CDR1, one in framework 2, one in CDR2, and one in CDR3 (FIG. 1B).
Mix-and-match of Heavy and Light Chains between HuAIP12 and HuAIP13

In order to determine if either the VH or VL region of HuAIP12 is responsible for HuAIP12' higher affinity binding to IP-10 in comparison to HuAIP13, the following two new antibodies were generated. The first antibody, designated 12H+13L, consisted of the HuAIP12 heavy chain and the HUAIP13 light chain. The second antibody, designated 13H+12L, consisted of the HuAIP13 heavy chain and the HuAIP12 light chain.

For expression of 12H+13L, the human gamma-1 heavy chain expression vector pVg1.D.Tt carrying the HuAIP12 VH (as described in Example 6) and the human kappa light chain expression vector pHuCkappa.rgpt.dE carrying the HuAIP13 VL (as described in Example 5) were cotransfected into human embryonic kidney cell line 293-H (Invitrogen™, Carlsbad, Calif.) using the Lipofectamine 2000™ reagent (Invitrogen™). For expression of 13H+12L, the pVg1.D.Tt vector carrying the HuAIP13 VH (as described in Example 5) and the pHuCkappargpt.dE vector carrying the HuAIP12 VL (Example 6) were cotransfected into 293-H cells using Lipofectamine 2000™ reagent. Similarly, HuAIP12 and HuAIP13 were expressed in 293-H cells using the corresponding expression vectors. Transiently expressed antibodies were purified with a protein A affinity column as described in Example 5. The purity of each of the purified antibodies analyzed by SDS-PAGE was more than 95%.

The binding affinities of the 12H+13L antibody and the 13H+12L antibody to human IP-10 were analyzed by competition ELISA as described in Example 5. The binding of AIP13 to human IP-10 was blocked by both the 12H+13L antibody and the 13H+12L antibody in a concentration-dependent manner. The $IC_{50}$ value for the 12H+13L antibody (3.0 µg/ml) was very similar to that for HuAIP12 (3.1 µg/ml), whereas the $IC_{50}$ value for the 13H+12L antibody (13.6 µg/ml) was even higher than that for HuAIP13 (9.2 µg/ml). This result indicates that it is the VH region of HuAIP12 that is important for high affinity binding to human IP-10.

Dissection of HuAIP12 VH

Since only the two amino acids at positions 55 and 104 (FIG. 1A) are different in the mature VH region between HuAIP12 and HuAIP13, two HuAIP12 VH variants were generated in order to identify which of the two amino acids is important for the high affinity of HuAIP12 to human IP-10. Site-directed mutagenesis was carried out in the HuAIP12 VH gene using the overlap-extension PCR method (Higuchi, R., 1989, in "PCR Technology: Principles and Applications for DNA Amplification", Erlich, H. A., ed., Stockton Press, New York, N.Y., pp 61-70). A first HuAIP12 VH variant designated T55I was generated by making a substitution from Thr to Ile at position 55 in the HuAIP12 VH (FIG. 1A). This T55I variant is depicted in SEQ ID NO. 78. A second HuAIP12 VH variant designated G104A was generated by making a substitution from Gly to Ala at position 104 in the HuAIP12 VH (FIG. 1A). This G104A variant is depicted in SEQ ID NO. 79. The T55I variant and the G104A variant were separately cloned into the gamma-1 heavy chain expression vector pVg1.D.Tt.(Cole, M. S., et al., J. Immunol. 159: 3613-3621 (1997)). Next, the T55I variant and the G104A variant were each expressed by cotransfection of the pVg1.D.Tt vector carrying the HuAIP12 VH T55I and G104A variant genes, respectively, and the light chain expression vector pHuCkappa.rgpt.dE (Kostelny, S. A., et al., Int. J. Cancer 93: 556-565 (2001)) carrying the unmodified HuAIP12 VL (SEQ ID NO. 48) into 293-H cells. Transiently expressed antibodies were purified by protein A column chromatography as described in Example 5. The purity of each of the purified antibodies analyzed by SDS-PAGE was more than 95%.

ELISA analysis of the binding affinities of the antibodies comprising the T55I and G104A variants.

The binding affinities of the HuAIP12 T55I and G104A variants were analyzed by competition ELISA as described in Example 5. Both the HuAIP12 T55I and the HuAIP12 G104A variants blocked the binding of AIP13 to human IP-10 in a concentration-dependent manner. The $IC_{50}$ value of the HuAIP12 G104A variant antibody was 59.5 µg/ml., while the $IC_{50}$ value of the original, unmodified HuAIP12 antibody was 4.1 µg/ml. Thus, the HuAIP12 G104A variant demonstrated a 14.5-fold decrease in binding affinity compared to the original, unmodified HuAIP12 antibody These results indicate that the presence of a glycine residue at position 104 is important for high affinity binding to IP-10. By contrast, the $IC_{50}$ value of the HuAIP12 T55I variant antibody was 1.6 µg/ml, which was even lower than that of unmodified HUAIP12 ($IC_{50}$ value=4.1 µg/ml), suggesting that a threonine residue at position 55 negatively influences the affinity of HuAIP12 to IP-10. The removal of a threonine residue by substitution with isoleucine at position 55 in the VH unexpectedly increased the affinity of HuAIP12 to human IP-10.

Biacore™ analysis of the binding affinities of the antibodies comprising the T55I and G104A variants.

The affinities of the unmodified HuAIP12, the T55I variant and the G104A variant were further characterized by surface plasmon resonance method using a Biacore 2000™ aparatus (Biacore Inc.™, Piscataway, N.J.). Goat anti-human IgG, γ chain specific antibody (GAHFc™; Jackson ImmunoResearch Laboratories, Inc.™, West Grove, Pa.) was immobilized on CM5™ sensor chips (Bioacore Inc.™) by amine coupling. HuAIP12 antibodies in HBS-P™ buffer (Bioacore Inc.™) containing 0.75 M NaCl were captured by GAHFc™ on the surface of a CM5 sensor chip by injection at a flow rate of 10 µl/minute for 1 minute. Human IP-10 (R&D Sytems, Inc.™, Minneapolis, Minn.) at concentrations ranging from 0.34 nM to 83.3 nM in HBS-P containing 0.75 M NaCl was then injected at a flow rate of 30 µl/minute for 4 minutes. Dissociation of IP-10 from the HuAIP12 antibody and the two variant antibodies was monitored for 11.7 minutes in HBS-P buffer. As a background control, IP-10 was directly injected onto a sensor chip immobilized with GAHFc, but without the step to capture test antibodies. Regeneration of the surface was performed by injection of 10 mM glycine (pH 1.9) for 1 minute. Data analysis was carried out using BIAevaluation™ software (Biacore Inc.™).

The observed association and dissociation constants (ka and kd, respectively) as well as calculated affinity equilibrium constants (Kd) are shown in Table 5.

TABLE 5

Affinity of HuAIP12 variants

| HuAIP12 antibody | ka (1/Ms) | kd (1/s) | n | Kd (M) |
| --- | --- | --- | --- | --- |
| Wild Type | $1.55 \times 10^6$ | $3.81 \times 10^{-4}$ | 3 | $2.51 \times 10^{-10}$ |
| T55I | $1.66 \times 10^6$ | $4.67 \times 10^{-5}$ | 3 | $2.69 \times 10^{-11}$ |
| G104A | $1.31 \times 10^5$ | $7.84 \times 10^{-4}$ | 3 | $5.98 \times 10^{-9}$ |

When compared to unmodified HuAIP12, the G104A variant had approximately 10-fold slower on-rate (ka) and 2-fold faster off-rate (kd). As a result, the affinity equilibrium constant (Kd) of the G104A variant (5.98 nM) is more than 20-fold higher than that of unmodified HuAIP12 (0.251nM), indicating that monovalent interaction of the G104A variant with IP-10 is 20-fold weaker than that of unmodified HuAIP12. On the other hand, the T55I variant had a similar on-rate and approximately 9-fold slower off-rate when compared to unmodified HuAIP12, resulting in more than 9-fold stronger affinity in monovalent interaction with IP-10, as measured by affinity equilibrium contant (Kd) (0.0269 nM). Although- the single amino acid substitution at position 55 in the T55I VH from threonine to isoleucine did not affect the on-rate in binding to IP-10, it significantly reduced the off-rate.

Thus, both the ELISA analysis and the Biacore™ apparatus analysis indicate that the HuAIP12 T55I variant antibody is a very high affinity anti-IP-10 monoclonal antibody. The HuAIP12 T55I VH amino acid sequence is depicted in SEQ ID NO. 78; the HuAIP12 T55I VL amino acid sequence (which is equivalent to the unmodified HuAIP12 VL amino acid sequence) is depicted in SEQ ID NO 48.

Example 9

This example describes the characterization of the high affinity anti-human IP-10 monoclonal antibody.

Characterization of HuAIP12 T55I by Chemotaxis Assay

The activity of HuAIP12 T55I to block the function of IP-10 was measured by a chemotaxis assay using a stable transfectant of a murine hematopoietic cell line Ba/F3 expressing human CXCR3 (Ba/F3-CXCR3). The chemotaxis experiments were carried out according to the procedure described in Example 4. Test antibodies at different concentrations were preincubated with 125 ng/ml of recombinant human IP-10 (R&D Systems™) in Chemotaxis buffer (RPMI-1640 containing 10% FBS) for 40 min at room temperature. Then, 30 μl of antibody-IP-10 mix was placed in the bottom chamber of the ChemoTx plate (Neuro Probe™, Gaithersburg, Md.) and 60 μl of Ba/F3-CXCR3 cells suspended in Chemotaxis buffer at 1×10$^6$/ml was placed in the filter-top well. After incubation for 90 min in a 7% $CO_2$ incubator at 37° C., non-migrating cells were removed by wiping the top of the filter with Kimwipes. Cells that had migrated to the bottom chamber through the filter were labeled with CellTiter-Glo™ (Promega™, Madison, Wis.). Luminescence of labeled cells was measured with a Packard LumiCount™ luninescent microplate reader (Meriden, Conn.).

As shown in FIG. 2, HuAIP12 T55I inhibited IP-10-mediated chemotaxis of Ba/F3-CXCR3 cells more efficiently than HuAIP12, indicating that HuAIP12 T55I, which has a higher affinity to human IP-10 than HuAIP12, neutralizes the function of IP-10 more strongly than HuAIP12.

Although the invention has been described with reference to the presently preferred embodiments, it should be understood that various modifications may be made without departing from the essence of the invention.

All publications, patents and patent applications cited herein are hereby incorporated by reference in their entirety to the same extent as if each individual publication, patent or patent application was specifically and individually indicated to be incorporated by reference in its entirety.

We claim:

1. An isolated anti-IP-10 antibody or antigen binding fragment which binds to the protein of SEQ ID NO: 1, wherein said antibody or antigen binding fragment comprises a heavy chain variable region comprising heavy chain complementarity determining regions (CDRs) of SEQ ID NO: 5, SEQ ID NO: 6, and SEQ ID NO: 74 and a light chain variable region comprising light chain CDRs of SEQ ID NO: 75, SEQ ID NO: 76, and SEQ ID NO: 77.

2. The isolated anti-IP-10 antibody or antigen binding fragment of claim 1 in which the heavy chain variable region comprises SEQ ID NO: 78.

3. The isolated anti-IP-10 antibody or antigen binding fragment of claim 1 in which the light chain variable region comprises SEQ ID NO: 46.

4. The isolated anti-IP-10 antibody or antigen binding fragment of claim 1 in which the heavy chain variable region comprises SEQ ID NO: 78 and the light chain variable region comprises SEQ ID NO: 46.

5. The isolated anti-IP-10 antibody according to claim 1, wherein said antibody is monoclonal.

6. The isolated anti-IP-10 antibody according to claim 1, wherein said antibody is a humanized antibody.

7. The isolated anti-IP-10 antibody according to claim 1, wherein said antibody is a chimeric antibody.

8. A pharmaceutical composition comprising the isolated anti-IP-10 antibody or antigen binding fragment of claim 1 and a physiologically acceptable pharmaceutical carrier.

9. A method of treating or reducing severity of at least one symptom of an inflammatory bowel disease in a subject in need thereof, comprising administering to said subject an effective amount of an isolated anti-IP-10 antibody or antigen binding fragment of claim 1, wherein said antibody or antigen binding fragment blocks the binding of CXCR3 to said SEQ ID NO: 1.

10. The method according to claim 9, wherein said inflammatory bowel disease is Crohn's disease.

11. The method according to claim 9, further comprising administering an immunosuppressive agent to the subject.

12. The method according to claim 9, wherein said inflammatory bowel disease is ulcerative colitis.

* * * * *